US006251666B1

(12) United States Patent
Beigelman

(10) Patent No.: US 6,251,666 B1
(45) Date of Patent: Jun. 26, 2001

(54) NUCLEIC ACID CATALYSTS COMPRISING L-NUCLEOTIDE ANALOGS

(75) Inventor: Leonid Beigelman, Longmont, CO (US)

(73) Assignee: Ribozyme Pharmaceuticals, Inc., Boulder, CO (US)

(*) Notice: Subject to any disclaimer, the term of this patent is extended or adjusted under 35 U.S.C. 154(b) by 0 days.

(21) Appl. No.: 09/048,825

(22) Filed: Mar. 25, 1998

Related U.S. Application Data

(60) Provisional application No. 60/042,464, filed on Mar. 31, 1997.

(51) Int. Cl.[7] .............................. C12N 5/00; C07H 21/02; C07H 21/04; C07H 21/00
(52) U.S. Cl. ..................... 435/325; 435/91.1; 536/23.1; 536/24.1; 536/25.3; 514/44
(58) Field of Search .................................. 435/91.1, 325; 436/501; 536/23.1, 24.1, 24.3–24.33, 25.3; 514/44; 935/77, 78

(56) References Cited

U.S. PATENT DOCUMENTS

| 4,987,071 | 1/1991 | Cech et al. ............................. 435/91 |
| 5,334,711 | 8/1994 | Sproat et al. ....................... 536/24.5 |
| 5,792,773 | * 8/1998 | Chu et al. ............................ 514/274 |

FOREIGN PATENT DOCUMENTS

| 89/02439 | 3/1989 | (WO) . |
| 0 360 257 | 3/1990 | (WO) . |
| 91/03162 | 3/1991 | (WO) . |
| 92/07065 | 4/1992 | (WO) . |
| 93/15187 | 8/1993 | (WO) . |
| 95/06731 | 3/1995 | (WO) . |
| 95/11910 | 5/1995 | (WO) . |
| 96/34879 | 11/1996 | (WO) . |

OTHER PUBLICATIONS

Scaringe et al., Nucleic Acids Res., vol. 18, No. 18, pp. 5433–5441, 1990.*
Wincott et al., Nucleic Acids Res., vol. 23, No. 14, pp. 2677–2684, 1995.*
Usman et al., Journal of the Sm. Chem. Soc., vol. 109, pp. 7845–7854, 1987.*
Abramovitz et al., "Catalytic role of 2'–hydroxyl groups within a group II intron active site," *Science* 271:1410–1413 (1996).
Ashley, "Modeling, synthesis, and hybridization properties of (L)–ribonucleic acid," *J. Am. Chem. Soc.* 114:9731–9736 (1992).
Azad et al., "Antiviral activity of a phosphorothioate oligonucleotide complementary to RNA of the human cytomegalovirus major immediate–early region," *Antimicrob. Agents Chemother* 37:1945–1954 (1993).
Banerjee et al., "The time dependence of chemical modification reveals slow steps in the folding of a group I ribozyme," *Biochemistry* 34(19):6504–6512 (1995).
Bartel and Szostak, "Isolation of New Ribozymes From a Large Pool of Random Sequences," *Science* 261:1411–1418 (1993).
Beaudry and Joyce, "Directed Evolution of an RNA Enzyme," *Science* 257:635–641 (1992).
Beaudry et al., "Minimum secondary structure requirements for catalytic activity of a self–splicing group I intron," *Biochemistry* 29:6534–6539 (1990).

(List continued on next page.)

*Primary Examiner*—Ardin H. Marschel
(74) *Attorney, Agent, or Firm*—McDonnell Boehnen Hulbert & Berghoff

(57) ABSTRACT

A nucleic acid catalyst comprising at least one L-nucleotide substitution.

30 Claims, 12 Drawing Sheets

L Nucleotide-Substituted Hammerhead Ribozyme

OTHER PUBLICATIONS

Been et al., "Secondary Structure of the Self–Cleaving RNA of Hepatitis Delta Virus: Applications to Catalytic RNA Design," *Biochemistry* 31:11843–11852 (1992).

Beigelman et al., "Synthesis of 2'–modified nucleotides and their incorporation into hammerhead ribozymes," *Nucleic Acids Research* 23(21):4434–4442 (1995).

Beigelman et al., "Chemical Modification of Hammerhead Ribozymes," *J. Biol. Chem.* 270:25702–25708 (1995).

Beigelman et al., "Synthesis of 1–Deoxy–D–Ribofuranose Phosphoramidite & The Incorporation of Abasic Nucleotides in Stem–Loop II of a Hammerhead Ribozyme," *Bioorganic & Medicinal Chemistry Letters* 4:1715–1720 (1994).

Benseler et al., "Hammerhead–like Molecules Containing Non–Nucleoside Linkers Are Active RNA Catalysts," *J. Am. Chem. Soc.* 115:8483–8484 (1993).

Berzal–Herranz et al., "Essential nucleotide sequences and secondary structure elements of the hairpin ribozyme," *EMBO J.* 12(6):2567–2573 (1993).

Berzal–Herranz et al., "In vitro selection of active hairpin ribozymes by sequential RNA–catalyzed cleavage and ligation reactions," *Genes and Dev.* 6(1):129–134 (1992).

Bevilacqua et al., "A mechanistic framework for the second step of splicing catalyzed by the Tetrahymena ribozyme," *Biochemistry* 35(2):648–58 (1996).

Bock et al., "Selection of single–stranded DNA molecules that bind and inhibit human thrombin," *Nature* 355:564–566 (1992).

Breaker, "Are engineered proteins getting competition from RNA?" *Current Opinion in Biotechnology* 7:442–448 (1996).

Breaker, "DNA Enzymes," *Nature Biotech* 15:427–431 (1997).

Breaker and Joyce, "Inventing and improving ribozyme function: rational design versus iterative selection methods," *TIBTECH* 12:268–275 (1994).

Burgin et al., "Chemically modified hammerhead ribozymes with improved catalytic rates," *Biochemistry* 35:14090–14097 (1996).

Cech, "Ribozymes and Their Medical Implications," *JAMA* 260:3030–3034 (1988).

Cech, "Ribozyme Engineering," *Current Opinion in Structural Biology* 2:605–609 (1992).

Chowrira et al., "Novel guanosine requirement for catalysis by the hairipin ribozyme," *Nature* 354:320–322 (1991).

Christoffersen and Marr, "Ribozymes as Human Therapeutic Agents," *J. Med. Chem.* 38:2023–2037 (1995).

Cload and Schepartz, "Polyether Tethered Oligonucleotide Probes," *J. Am. Chem. Soc.* 113:6324–6326 (1991).

Daniels et al., "Two competing pathways for self–splicing by group II introns: a quantitative analysis of in vitro reaction rates and products," *J. Mol. Biol.* 256(1):31–39 (1996).

De Clercq et al., "The antiviral activity of thiophosphate–substituted polyribonucleotides in vitro and in vivo," *Virology* 42:421–428 (1970).

Divakar et al., "4–(1,2,4–triazol–1–yl)–and 4–(3–nitro–1,2, 4–triazol–1–yl)–1–(β–D–2,3,5–tri–O–acetylarabinofuranosyl) pyrimidin–2(1H)–ones. Valuable intermediates in the synthesis of derivatives of 1–(β–D–arabinofuranosyl) cytosine (Ara–C)," *J. Chem. Soc. Perkin I* 1171 (1982).

Durand et al., "Circular Dichroism Studies of an Oligodeoxyribonucleotide Containing a Hairpin Loop Made of a Hexaethylene Glycol Chain: Conformation and Stability," *Nucleic Acids Research* 18:6353–6359 (1990).

Ferentz and Verdine, "Disulfied Cross–Linked Oligonucleotides," *J. Am. Chem. Soc.* 113:4000–4002 (1991).

Forster and Altman, "External guide sequences for an RNA enzyme," *Science* 249:783–786 (1990).

Gao et al., "Phosphorothioate oligonucleotides are inhibitors of human DNA polymerases and Rnase H: Implications for antisense technology," *Molec. Pharmac.* 41:223–229 (1992).

Grasby et al., "Purine Functional Groups in Essential Residues of the Hairpin ribozyme Required for Catalytic Cleavage of RNA," *Biochemistry* 34(12):4068–4076 (1995).

Griffin et al., "Group II intron ribozymes that cleave DNA and RNA linkages with similar efficiency, and lack contacts with substrate 2'–hydroxyl groups," *Chem Biol.* 2:761–770 (1995).

Guerrier–Takada et al., "The RNA Moiety of Ribonuclease P Is the Catalytic Subunit of the Enzyme," *Cell* 35:849–857 (1983).

Guo and Collins, "Efficient trans–cleavage of a stem–loop RNA substrate by a ribozyme derived from neurospora VS RNA," *EMBO J.*, 14(2):368–376 (1995).

Hampel and Tritz, "RNA Catalytic Properties of the Minimum (–)s TRSV Sequence," *Biochemistry* 28:4929–4933 (1989).

Hampel et al., "'Hairpin' catalytic RNA model: evidence for helices and sequence requirement for substrate RNA," *Nucleic Acids Res.* 18:299–304 (1990).

Harris and Pace, "Identification of phosphates involved in catalysis by the ribozyme RNase P RNA," *RNA* 1(2):210–218 (1995).

Haseloff and Gerlach, "Simple RNA Enzymes with New and Highly Specific Endoribonuclease Activities," *Nature* 334:585–591 (1988).

Hendry et al., "Using linkers to investigate the spatial separation of the conserved nucleotides $A_g$ and $G_{12}$ in the hammerhead ribozyme," *Biochimica et Biophysica Acta* 1219:405–412 (1994).

Herschlag et al., "Catalysis of RNA cleavage by the Tetrahymena thermophila ribozyme. 2. Kinetic description of the reaction of an RNA substrate that forms a mismatch at the active site," *Biochemistry* 29(44):10172–10180 (1990).

Hobbs et al., "A general method for the synthesis of 2'–azido–2'–deoxy– and 2'–amino–2'–deoxyribofuranosyl purines," *J. Org. Chem* 42:714–719 (1977).

Holy, "Nucleic acid components and their analogues. CLIII. Preparation of 2'–deoxy–L–ribonucleosides of the pyrimidine series," *Coll. Czech. Chem. Commun.* 4072–4087 (1972).

Jacques et al., *Enantiomers, Racemates, and Resolutions*, Krieger Publishing Co., Florida, USA, pp. 1–31 (1981).

Jeffries and Symons, "A Catalytic 13–mer Ribozyme," *Nucl. Acids Res.* 17:1371–1377 (1989).

Joseph et al., "Substrate selection rules for the hairpin ribozyme determined by in vitro selection, mutation, and analysis of mismatched substrates," *Genes Dev.* 7(1):130–138 (1993).

Joyce, "Amplification, mutation and selection of catalytic RNA," *Gene* 82:83–87 (1989).

Joyce, "Directed Molecular Evolution," *Scientific American* 267:90–97 (1992).

Jaschke et al., "Automated incorporation of polyethylene glycol into synthetic oligonucleotides," *Tetrahedron Lett.* 34:301–304 (1993).

Klubmann et al., "Mirror–image RNA that binds D–adenosine," *Nature Biotech.* 14:1112–1115 (1996).

Knitt et al., "pH Dependencies of the Tetrahymena Ribozyme Reveal an Unconventional Origin of an Apparent pKa," *Biochemistry* 35(5):1560–70 (1996).

Kumar and Ellington, "Artificial evolution and natural ribozymes," *FASEB J.* 9:1183–1195 (1995).

Li et al., "Thermodynamic and activation parameters for binding of a pyrene–labeled substrate by the Tetrahymena ribozyme: docking is not diffusion–controlled and is driven by a favorable entropy change," *Biochemistry* 34:14394–143949 (1995).

Limbach et al., "Summary: the modified nucleosides of RNA," *Nucleic Acids Research* 22(12):2183–2196 (1994).

Ruffner et al., "Sequence Requirements of the Hammerhead RNA Self–Cleavage Reaction," *Biochemistry* 29:10695–10702 (1990).

Saville and Collins, "A Site–Specific Self–Cleavage Reaction Performed by a Novel RNA In Neurospora Mitochondria," *Cell* 61:685–696 (1990).

Saville and Collins, "RNA–Mediated Ligation of Self–Cleavage Products of a Neurospora Mitochondrial Plasmid Transcript," *Proc. Natl. Acad. Sci. USA* 88:8826–8830 (1991).

Schmidt et al., "Base and sugar requirements for RNA cleavage of essential nucleoside residues in internal loop B of the hairpin ribozyme: implications for secondary structure," *Nucleic Acids Res.* 24(4):573–581 (1996).

Shaw et al., "Modified deoxyoligonucleotides stable to exonuclease degradation in serum," *Nucleic Acids Research* 19:747–750 (1991).

Strobel et al., "Minor groove recognition of the conserved Gcntdot.U pair at the Tetrahymena ribozyme reaction site," *Science* 267(5198):675–679 (1995).

Strobel et al., "Exocyclic Amine of the Conserved G.cntdot.U Pair at the Cleavage Site of the Tetrahymena Robozyme Contributes to 5'–Splice Site Selection and Transition StateStabilization," *Biochemistry* 35(4):2101–1211 (1996).

Sugiyama et al., "Catalytic activities of hammerhead ribozymes with a triterpenoid linker instead of stem/loop II," *FEBS Lett.* 392:215–219 (1996).

Sullenger and Cech, "Ribozyme–mediated repair of defective mRNA by targeted trans–splicing," *Nature* 371:619–622 (1994).

Szostak, "In Vitro Genetics," *TIBS* 17:89–93 (1993).

Tazawa et al., "L–Adenylyl–(3'–5')–L–adenosine and L–Adenylyl–(2'–5')–L–adenosine," *Biochemistry* 9:3499–3514 (1970).

Thompson et al., "In vitro selection of hammerhead ribozymes containing a bulged nucleotide in stem II," *Nucl. Acids Res.* 24:4401–4406 (1996).

Ti et al., "Transient protection: Efficient one–flask syntheses of protected deoxynucleosides," *J. Am. Chem. Soc.* 104:1316–1319 (1982).

Uhlenbeck "A Small Catalytic Oligoribonucleotide," *Nature* 328:596–600 (1987).

Usman and Cedergren, "Exploiting the chemical synthesis of RNA," *Trends In Biochem. Sci.* 17:334–339 (1992).

Usman et al., "Chemical modification of hammerhead ribozymes: activity and nuclease resistance," *Nucleic Acids Syposium Series* 31:163–164 (1994).

Usman and McSwiggen, "Ch. 30—Catalytic RNA (Ribozymes) as Drugs," *Ann. Rep. Med. Chem.* 30:285–294 (1995).

Verheyden et al., "Synthesis of Some Pyrimidine 2'–Amino–'–deoxynucleosides," *J. Org. Chem.* 36:250–254 (1971).

Visser et al., "Synthesis of the mirror image of the RNA fragment D–CAAGG: A model compound to study interactions between oligonucleotides of opposite handedness," *Recl. Trav. Pays–Bas* 105:582–537 (1986).

Vorbruggen et al., "Nucleoside Synthesis with Trimethylsilyl Triflate and Perchlorate as Catalysts," *Chem. Ber.* 114:1234–1255 (1981).

Yuan et al., "Targeted cleavage of mRNA by human RNase P., " *Proc. Natl. Acad. Sci. USA* 89:8006–8010 (1992).

Zarrinkar et al., "The P9.1–P9.2 peripheral extension helps guide folding of the Tetrahymena ribozyme," *Nucleic Acids Res.* 24(5):854–858 (1996).

Zaug et al., "The Tetrahymena Ribozyme Acts Like an RNA Restriction Endonuclease," *Nature* 324:429–433 (1986).

Zimmerly et al., "A group II intron RNA is a catalytic component of a DNA endonuclease involved in intron mobility," *Cell* 83(4):529–538 (1995).

Lisacek et al., "Automatic identification of group I intron cores in genomic DNA sequences," *J. Mol. Biol.* 235(4):1206–1217 (1994).

Long et al. "Kinetic characterization of intramolecular and intermolecular hammerhead RNAs with stem II deletions," Proc. Natl. Acad. Sci. 91:6977–6981 (1994).

Ma et al., "Design and Synthesis of RNA Miniduplexes via a Synthetic Linker Approach," *Biochemistry* 32:1751–1758 (1993).

Ma et al., "Design and Synthesis of RNA Miniduplexes via a Synthetic Linker Approach. 2. Generation of Covalently Closed, Double–Stranded Cyclic HIV–1, TAR RNA Analogs with High Tat–Binding Affinity," *Nucleic Acids Research* 21:2585–2589 (1993).

Marti et al., "Oligodeoxyribonucleotide phosphorothioate fluxes and localization in hematopoietic cells," *Antisense Res. Dev.* 2:27–39 (1992).

McCall et al., "Minimal sequence requirements for ribozyme activity," *Proc. Natl. Acad. Sci. USA* 89:5710–5714 (1992).

McCurdy et al., "Deoxyoligonucleotides with Inverted Polarity: Synthesis and Use in Triple–Helix Formation" *Nucleosides & Nucleotides* 10:287–290 (1991).

Michael et al., "Slippery substrates," *Nat. Struct. Biol.* 1(1):5–7 (1994).

Michel et al., "Structure and activities of group II introns," *Annu. Rev. Biochem.* 64:435–461 (1995).

Michels and Pyle, "Conversion of a Group II Intron into a New Multiple–Turnover Ribozyme that Selectivity Cleaves Oligonucleotides: Elucidation of Reaction Mechanism and Structure/Function Relationships," *Biochem.* 34(9):2965–2977 (1995).

Milligan and Uhlenbeck, "Synthesis of Small RNAs Using T7 RNA Polymerase," *Methods Enzymol.* 180:51–62 (1989).

Mohr et al., "A tyrosyl–TrnA synthetase can function similarly to an RNA structure in the Tetrahymena ribozyme," *Nature* 370:147–150 (1994).

Nathans et al., "Restriction endonucleases in the analysis and restructuring of DNA molecules," *Ann. Rev. Bochem.* 44:273–293 (1975).

Nolte et al., "Mirror–design of L–oligonucleotide ligands binding to L–arginine," *Nature Biotech.* 14:1116–1119 (1996).

Ono et al., "DNA Triplex Formation of Oligonucleotide Analogues Consisting of Linker Groups and Octamer Segments That Have Opposite Sugar–Phosphate Backbone Polarities," *Biochemistry* 30:9914–9921 (1991).

Orgel, "Selection in vitro," *Proc. R. Soc. London B.* 205:435–442 (1979).

Pan et al., "Properties of an in vitro selected $Pb^{2+}$ cleavage motif," *Biochemistry* 33:9561–9565 (1994).

Pan et al., "Probing of tertiary interactions in RNA: 2'–hydroxyl–base contacts between the RNase P RNA and pre–tRNA," *Proc. Natl. Acad. Sci. U.S.A.* 92(26):12510–12514 (1995).

Perez et al., "Sequence–independent induction of Sp1 transcription factor activity by phosphorothioate oligodeoxynucleotides," *Proc. Natl Acad Sci. U.S.A.* 91:5957–5961 (1994).

Perreault et al., "Mixed Deoxyribo–and Ribo–Oligonucleotides with Catalytic Activity," *Nature* 344:565–567 (1990).

Perrotta and Been, "Cleavage of oligoribonucleotides by a ribozyme derived from the hepatitis δ virus RNA sequence," *Biochemistry* 31:16–21 (1992).

Perotta and Been, "A pseudoknot–like structure required for efficient self–cleavage of hepatitis delta virus RNA," *Nature* 350:434–436 (1991).

Pieken et al., "Kinetic Characterization of Ribonuclease–Resistant 2'–Modified Hammerhead Ribozymes," *Science* 253:314–317 (1991).

* cited by examiner

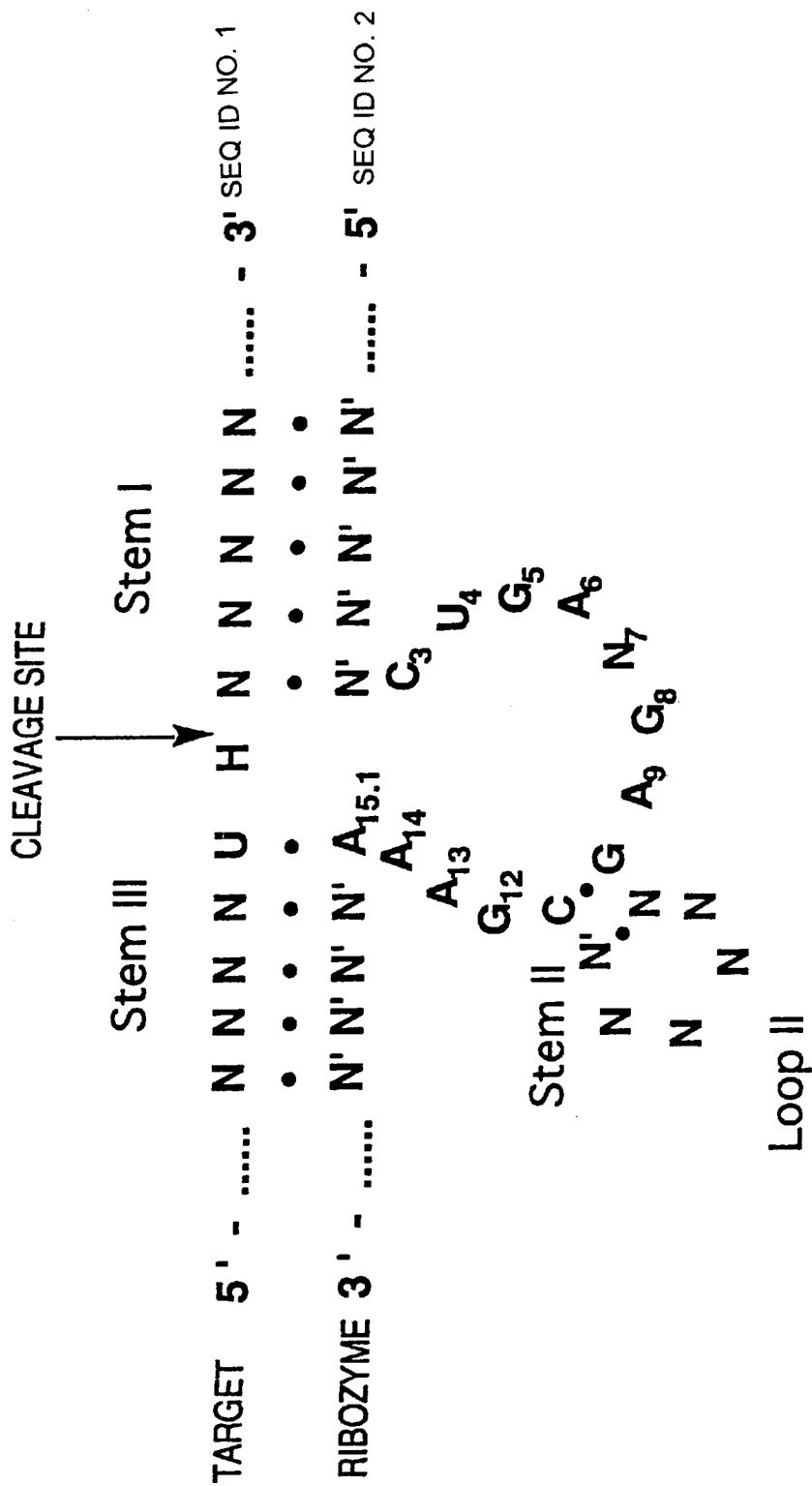
FIGURE 1: The Hammerhead Ribozyme

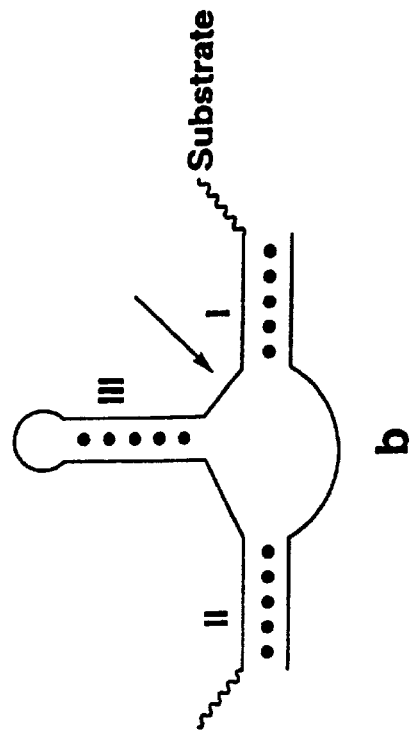
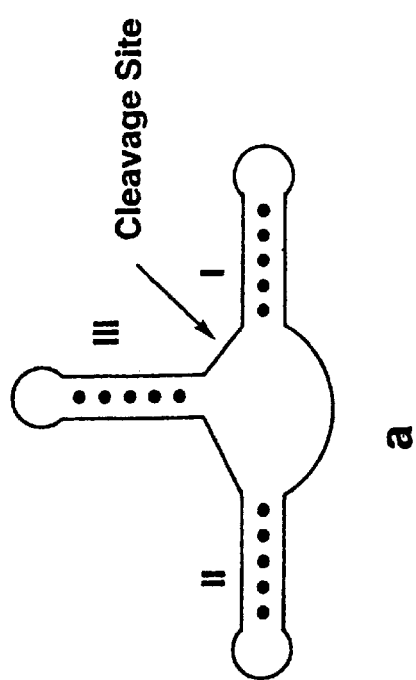
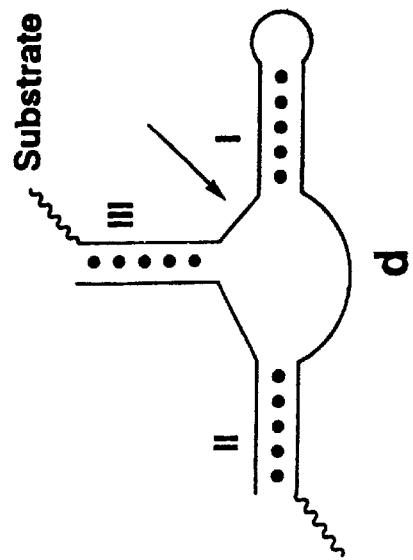
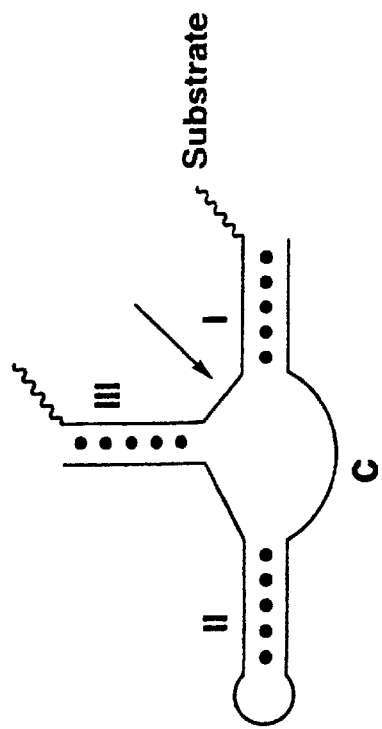
FIGURE 2: Hammerhead Ribozyme Substrate Motifs

FIGURE 3: Hairpin Ribozyme
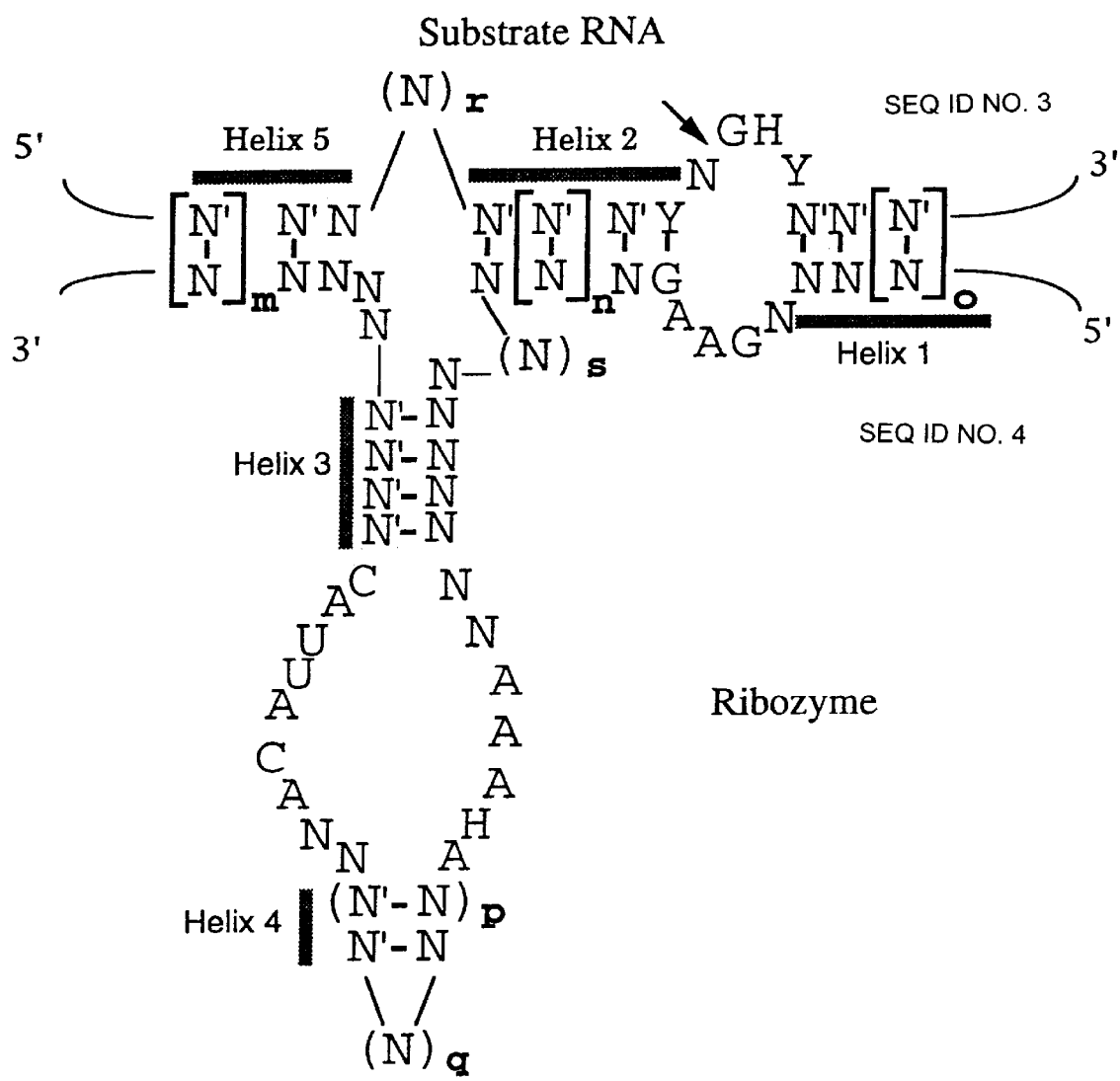

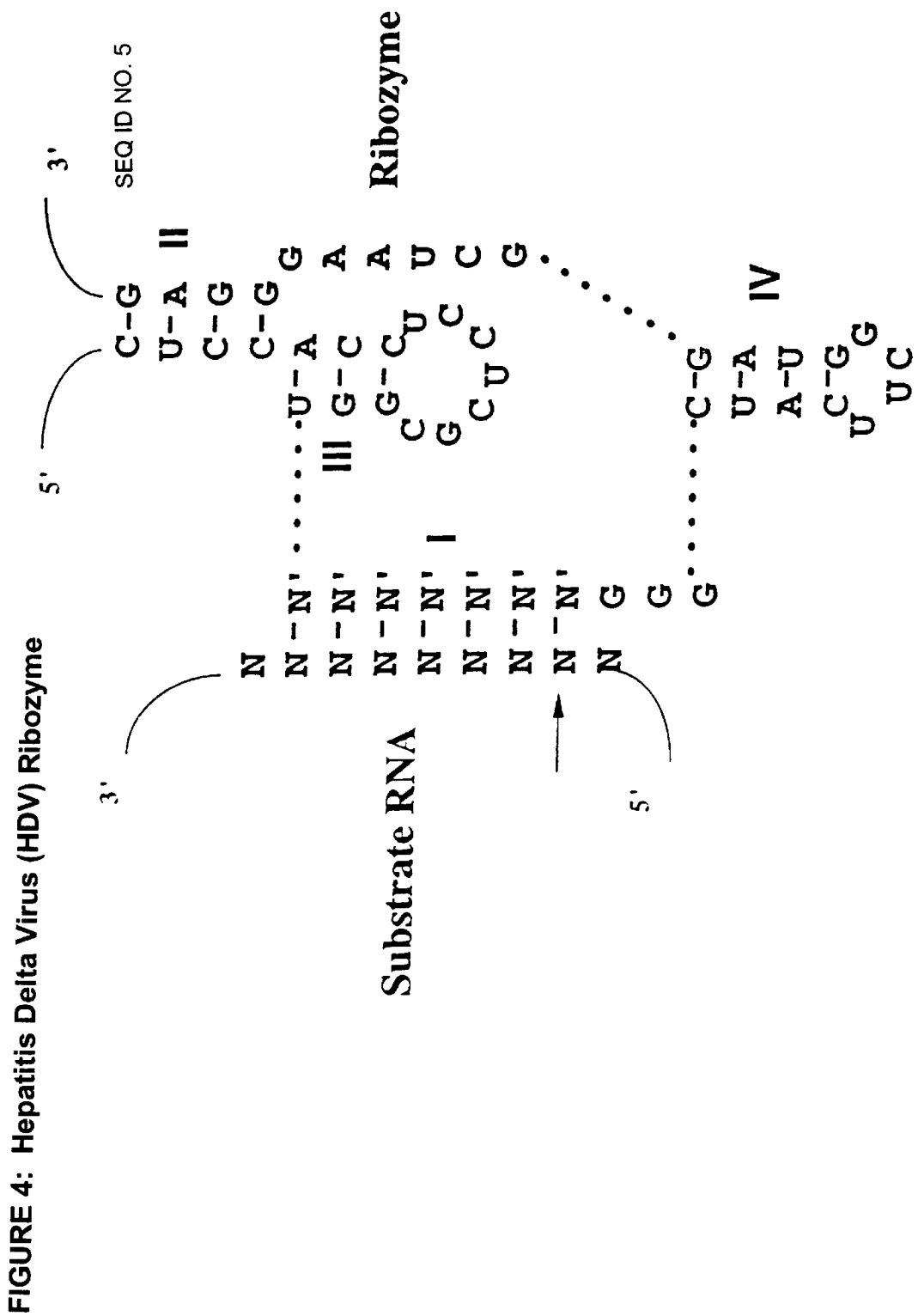
FIGURE 4: Hepatitis Delta Virus (HDV) Ribozyme

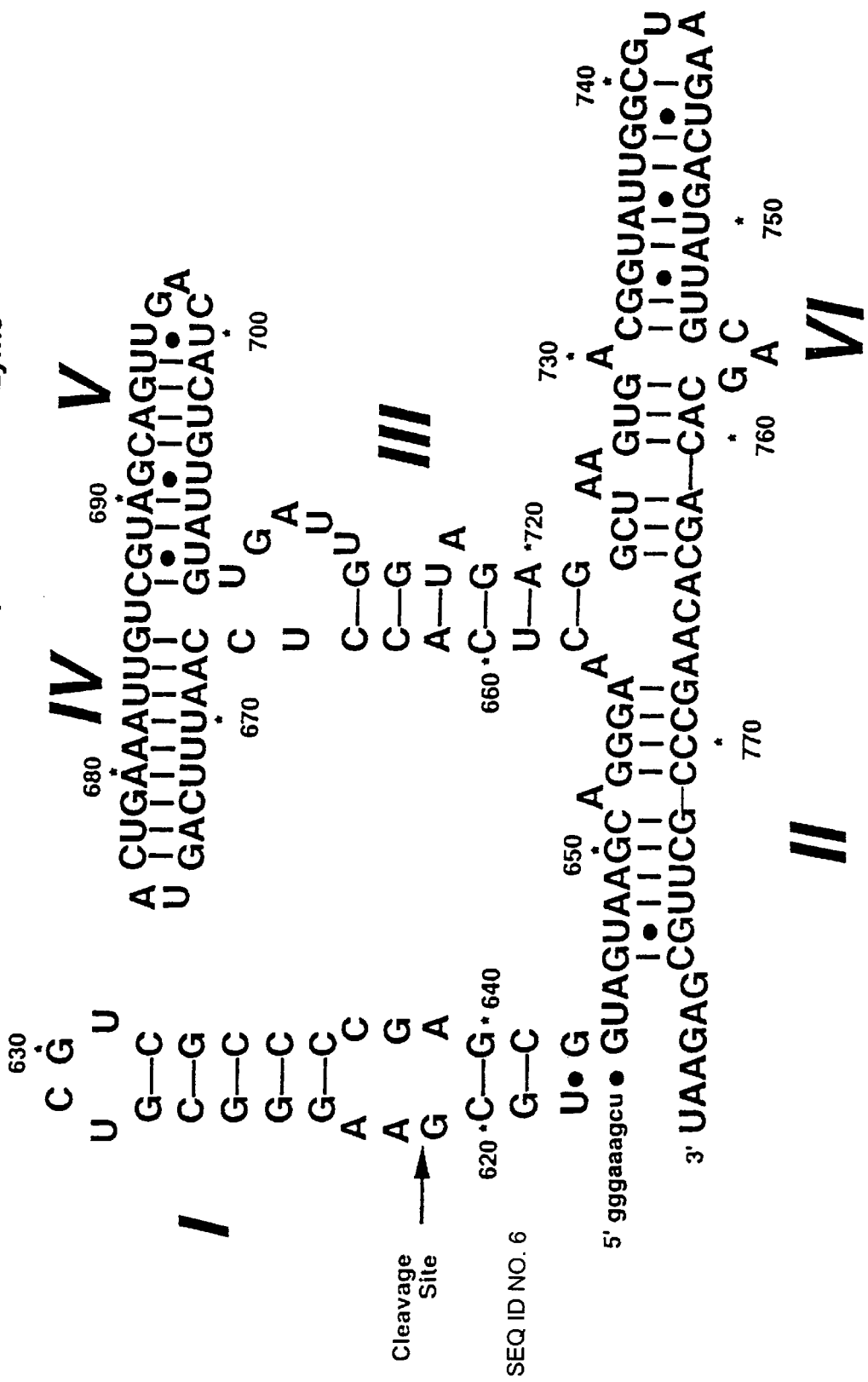
FIGURE 5: Neurospora vs RNA Enzyme

Figure 6: D- and L- Nucleotides
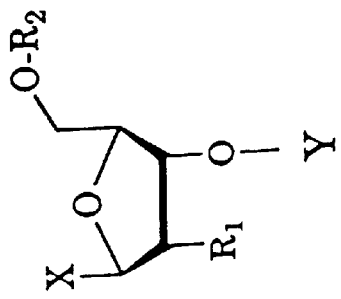
L-Nucleotides
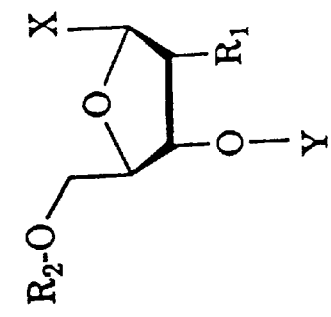
D-Nucleotides
X = nucleic acid base or H
Y = phosphorus-containing group
$R_2$ = blocking group or a phosphorus-containing group
$R_1$ = H, OH or any other 2'-substitution

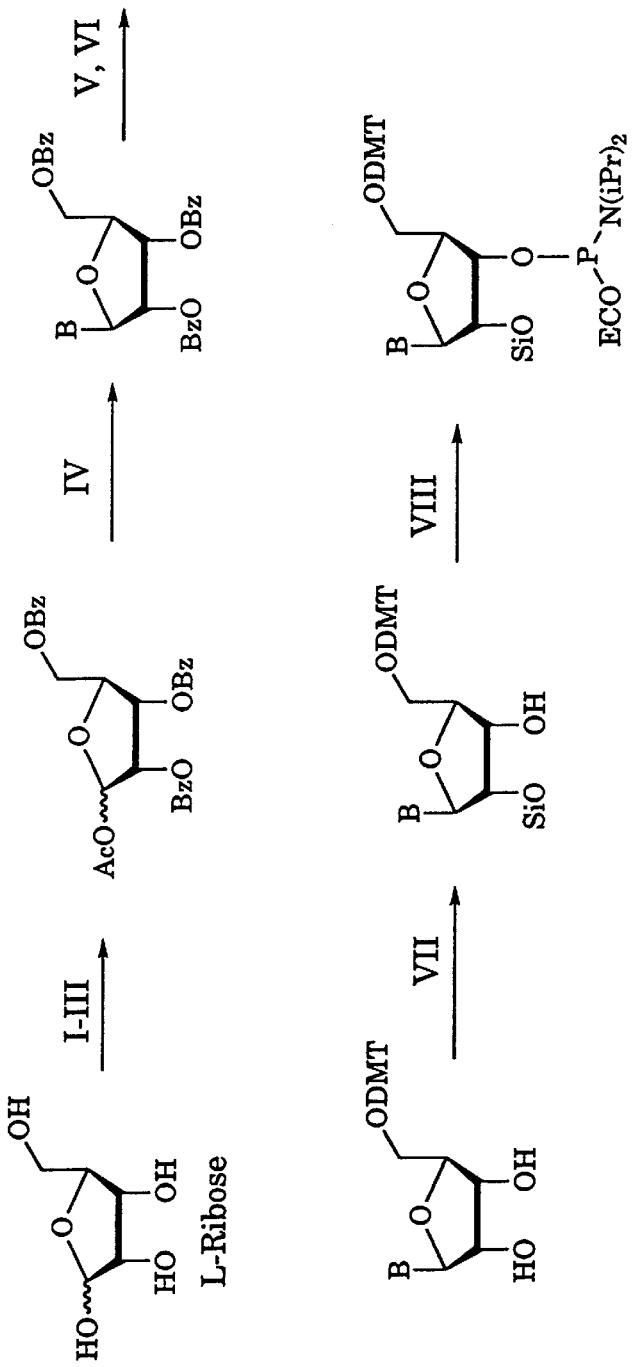
Figure 7: Synthesis of L-Ribonucleoside Phosphoramidites (Scheme 1)
B = protected nucleic acid base or H
I. MeOH,H+ II. BzCl/Py III. AcOH,Ac2O,H2SO4; IV. B$^{tms}$,CF3SO3SiMe3; V. NaOMe/MeOH Dowex 50 Py+; VI. DMTCl/Py; VII. TBDMSiCl/AgNO3; CIP(OCE)(NiPr2)

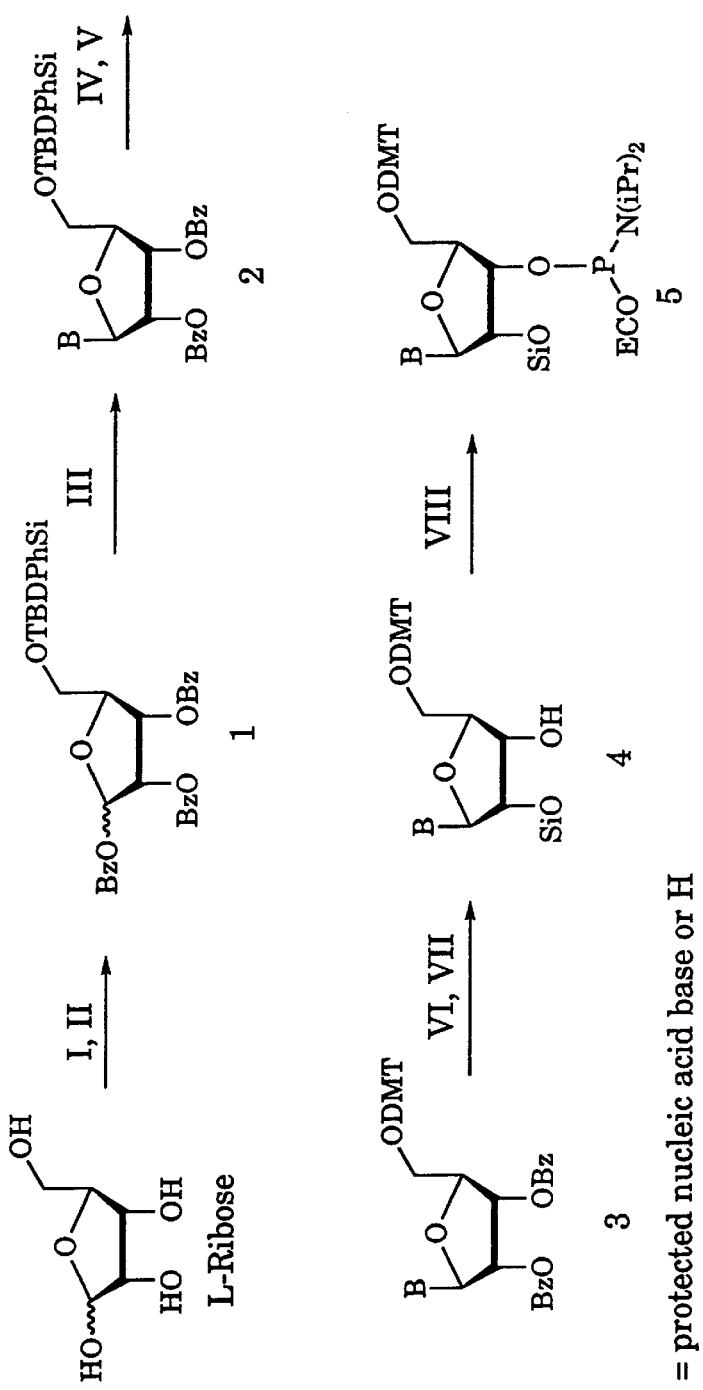
Figure 8: Synthesis of L-Ribonucleoside Phosphoramidites from L-Ribose using 5-O-Silyl protection (Scheme 2)

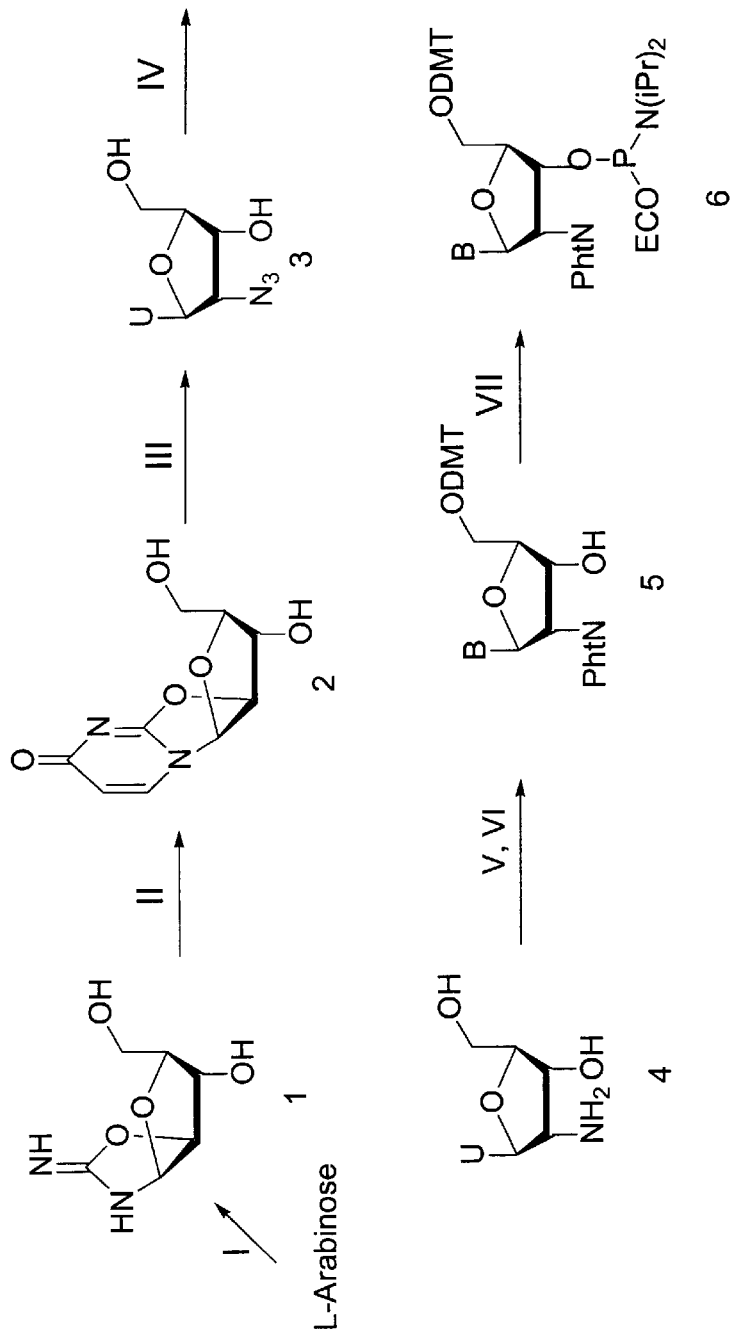

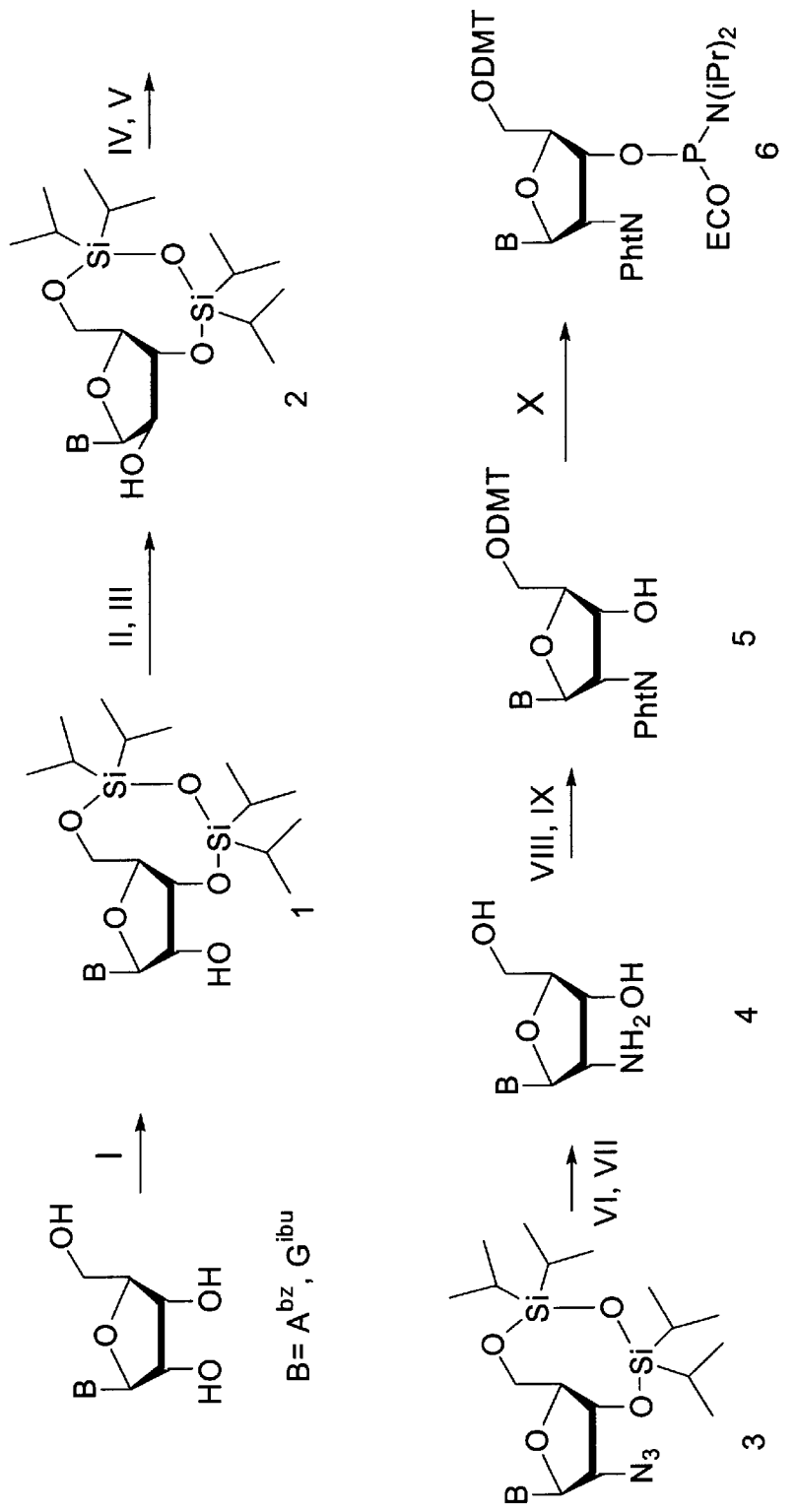
*Figure 9B: Synthesis of 2'-amino-2'-deoxy-L-Purine nucleoside Phosphoramidites*
I. TIPSiCl$_2$/Py; II. CrO$_3$/Py, Ac$_2$O; III. Na(OAc)$_3$BH; IV. TfCl/DMAP; V. LiN$_3$/DMF; VI. Ph$_3$P/NH$_4$OH; VII. TBAF; VIII. Nefkin's reagent; IX. DMTCl/Py; X. phosphitylation

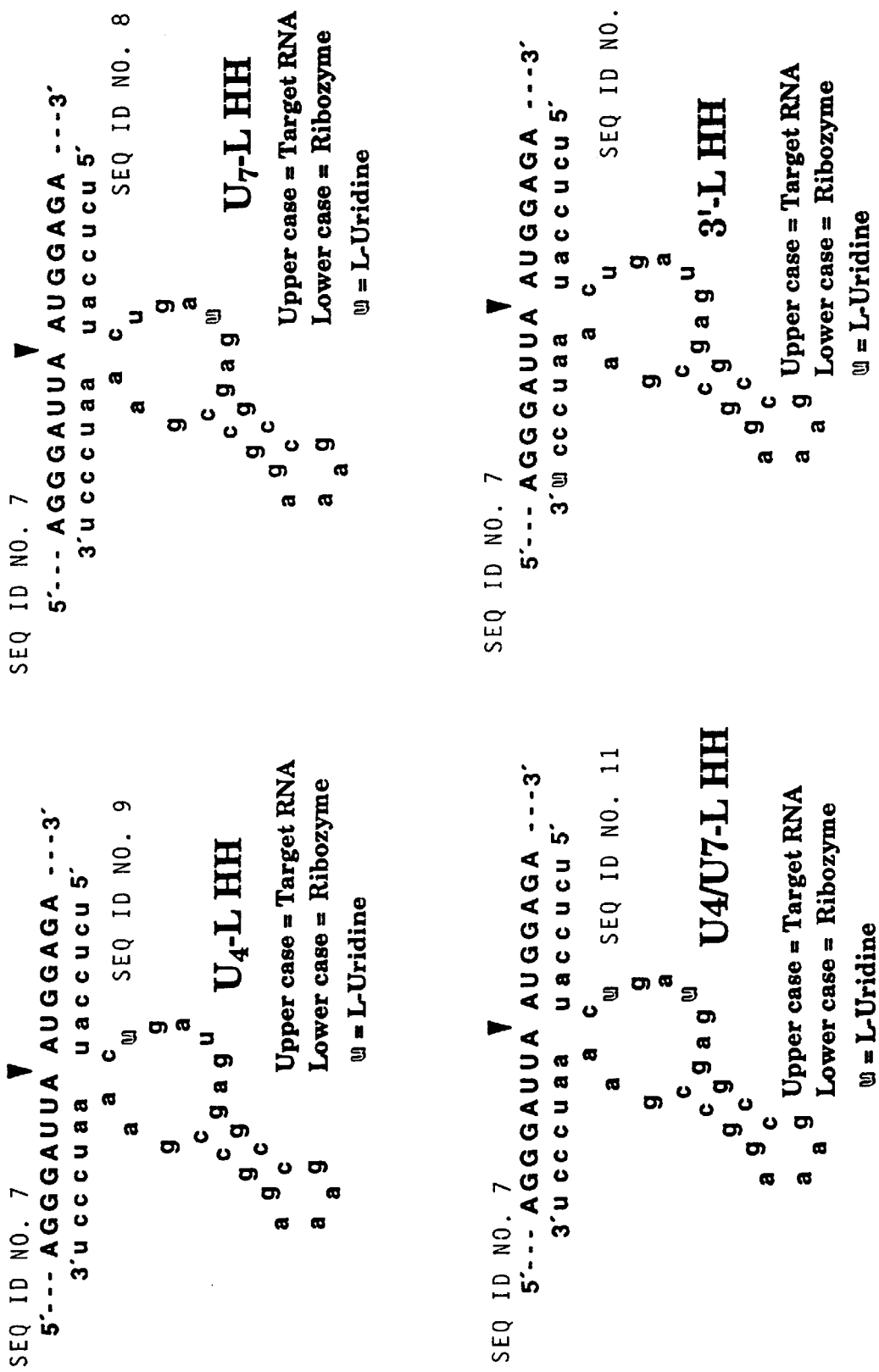
FIGURE 10: L Nucleotide-Substituted Hammerhead Ribozyme

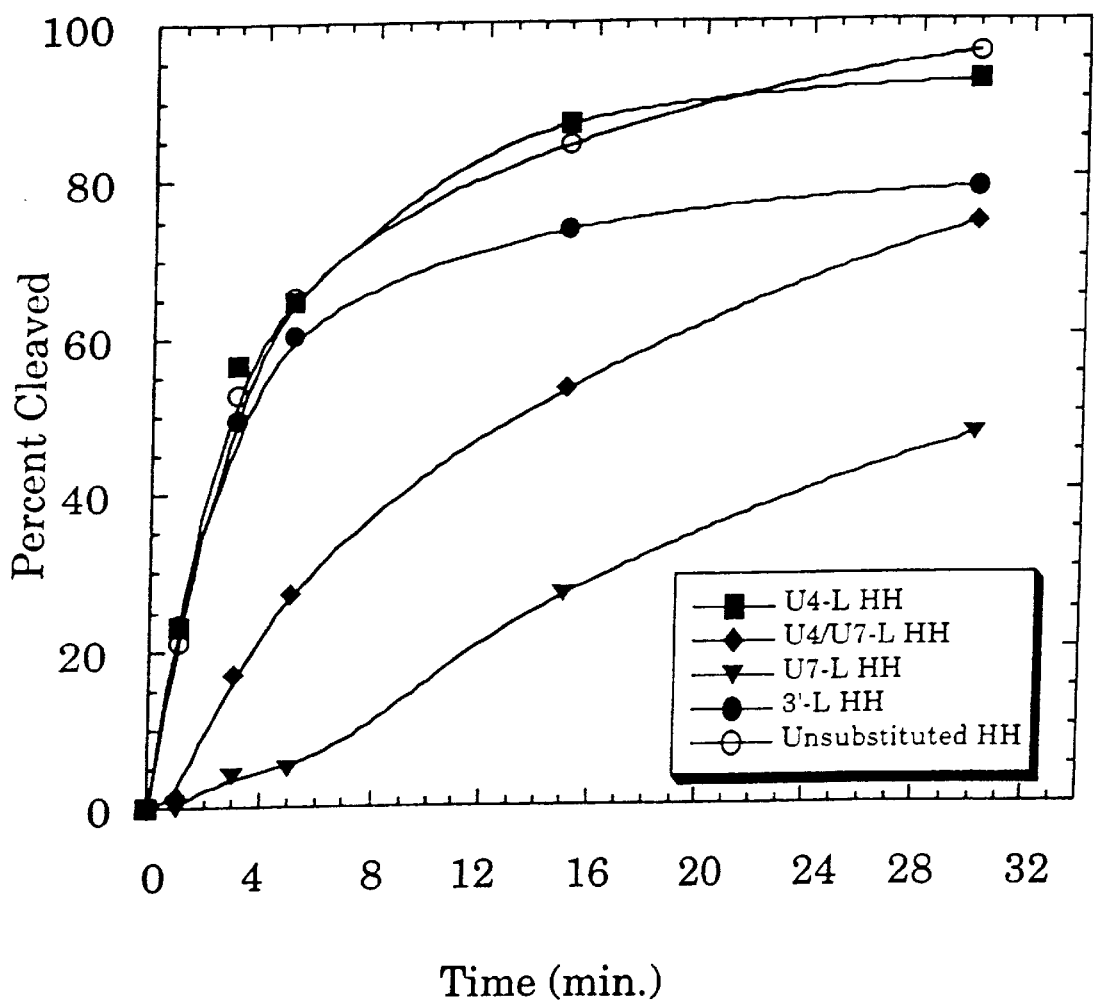
FIGURE 11: RNA Cleavage Catalyzed by L Nucleotide Substituted Ribozymes

NUCLEIC ACID CATALYSTS COMPRISING L-NUCLEOTIDE ANALOGS

CROSS-REFERENCE TO RELATED APPLICATIONS

This application claims the benefit of U.S. Provisional Application 60/042,464 entitled "Nucleic Acid Catalysts Comprising L-Nucleotide Analogs" filed Mar. 31, 1997 now abandoned, which is hereby incorporated herein by reference in its entirety, including any drawings and figures.

BACKGROUND OF THE INVENTION

This invention relates to chemically synthesized ribozymes, or enzymatic nucleic acid molecules and derivatives thereof.

The following is a brief description of nucleic acid catalysts. This summary is not meant to be complete but is provided only for understanding of the invention that follows. This summary is not an admission that all of the work described below is prior art to the claimed invention.

Nucleic acid catalysts are nucleic acid molecules capable of catalyzing one or more of a variety of reactions including the ability to repeatedly cleave other separate nucleic acid molecules in a nucleotide base sequence-specific manner. Such enzymatic nucleic acid molecules can used, for example, to target virtually any RNA transcript (Zaug et al., 324, *Nature* 429 1986; Cech, 260 *JAMA* 3030, 1988; and Jefferies et al., 17 *Nucleic Acids Research* 1371, 1989).

Because of their sequence-specificity, trans-cleaving enzymatic nucleic acid molecules show promise as therapeutic agents for human disease (Usman & McSwiggen, 1995 *Ann. Rep. Med. Chem.* 30, 285–294; Christoffersen and Marr, 1995 *J. Med. Chem.* 38, 2023–2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

There are seven basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

In addition, several in vitro selection (evolution) strategies (Orgel, 1979, *Proc. R. Soc. London,* B 205, 435) have been used to evolve new nucleic acid catalysts capable of catalyzing a variety of reactions, such as cleavage and ligation of phosphodiester linkages and amide linkages, (Joyce, 1989, *Gene,* 82, 83–87; Beaudry et al., 1992, *Science* 257, 635–641; Joyce, 1992, *Scientific American* 267, 90–97; Breaker et al., 1994, *TIBTECH* 12, 268; Bartel et al., 1993, *Science* 261:1411–1418; Szostak, 1993, *TIBS* 17, 89–93; Kumar et al., 1995, *FASEB J.,* 9, 1183; Breaker, 1996, *Curr. Op. Biotech.,* 7, 442).

The enzymatic nature of a ribozyme is advantageous over other technologies, since the effective concentration of ribozyme necessary to effect a therapeutic treatment is generally lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base-pairing. Thus, it is thought that the specificity of action of a ribozyme is greater than that of antisense oligonucleotide binding the same RNA site.

The development of ribozymes that are optimal for catalytic activity would contribute significantly to any strategy that employs RNA-cleaving ribozymes for the purpose of regulating gene expression. The hammerhead ribozyme functions with a catalytic rate ($k_{cat}$) of ~1 min$^{-1}$ in the presence of saturating (10 mM) concentrations of Mg$^{2+}$ cofactor. However, the rate for this ribozyme in Mg$^{2+}$ concentrations that are closer to those found inside cells (0.5–2 mM) can be 10- to 100-fold slower. In contrast, the RNase P holoenzyme can catalyze pre-tRNA cleavage with a $k_{cat}$ of ~30 min$^{-1}$ under optimal assay conditions. An artificial 'RNA ligase' ribozyme has been shown to catalyze the corresponding self-modification reaction with a rate of ~100 min$^{-1}$. In addition, it is known that certain modified hammerhead ribozymes that have substrate binding arms made of DNA catalyze RNA cleavage with multiple turn-over rates that approach 100 min$^{-1}$. Finally, replacement of a specific residue within the catalytic core of the hammerhead with certain nucleotide analogs gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain self-cleaving ribozymes may not be optimized to give maximal catalytic activity, or that entirely new RNA motifs could be made that display significantly faster rates for RNA phosphoester cleavage.

Chemically-modified ribozymes can be synthesized which are stable in human serum for up to 260 hours (Beigelman et al., 1995, *J. Biol. Chem.,* 270, 25702) and maintain near wild type (chemically unmodified equivalent of modified ribozyme) activity in vitro. A number of laboratories have reported that the enhanced cellular efficacy of phosphorothioate-substituted antisense molecules. The enhanced efficacy appears to result from either i) increased resistance to 5'-exonuclease digestion (De Clercq et al., 1970 *Virology* 42, 421–428; Shaw et al., 1991 *Nucleic Acids Res.* 19, 747–750), ii) intracellular localization to the nucleus (Marti et al., 1992 *Antisense Res. Dev.* 2, 27–39), or iii) sequence-dependent non-specific effects (Gao et al., 1992 *Molec. Pharmac.* 41, 223–229; Bock et al., 1992 *Nature* 355, 564–566; and Azad, et al., 1993 *Antimicrob. Agents Chemother.* 37, 1945–1954) which are not manifested in non-thioated molecules. Many effects of thioated compounds are probably due to their inherent tendency to associate non-specifically with cellular proteins such as the Sp1 transcription factor (Perez et al., 1994 *Proc. Natl Acad Sci. U.S.A.* 91, 5957–5961). Chemical modification of enzymatic nucleic acids that provide resistance to cellular nuclease digestion without reducing the catalytic activity or cellular efficacy will be important for in vitro and in vivo applications of ribozymes.

The references cited above are distinct from the presently claimed invention since they do not disclose and/or contemplate the enzymatic nucleic acid molecules of the instant invention.

SUMMARY OF THE INVENTION

This invention relates to nucleic acid catalysts with one or more L-nucleotide-substitutions. These substitutions alone or in combination with other D- and L-chemical substitutions protect the nucleic acids from nuclease degradation without entirely inhibiting their catalytic activity. Resistance to nuclease degradation can increase the half-life of these nucleic acids inside a cell and improve the overall effectiveness of nucleic acid catalysts. These modifications may also be used to facilitate efficient uptake of nucleic acid catalysts by cells, transport and localization of these nucleic acids within a cell, and help achieve an overall improvement in the efficacy of nucleic acid catalysts in vitro and in vivo.

The term "chemical substitution" as used herein refers to any base, sugar and/or phosphate modification that will protect the nucleic acids from degradation by nucleases without inhibiting their catalytic activity entirely.

In a preferred embodiment, the invention features a nucleic acid catalyst comprising at least one L-nucleotide, wherein the L-nucleotide has the formula I:

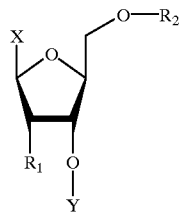

wherein, X is a nucleic acid base, which may be modified or unmodified, or H; Y is a phosphorus-containing group; R1 is H, OH or other 2'-modifications; R2 is a blocking group or a phosphorus-containing group.

A "blocking group" is a group which is able to be removed after polynucleotide synthesis and/or which is compatible with solid phase polynucleotide synthesis.

A "phosphorus containing group" can include phosphorus in forms such as dithioates, phosphoramidites and/or as part of an oligonucleotide.

In one preferred embodiment the invention features a nucleic acid catalyst made up entirely of L-nucleotides of Formula I and has no D-nucleotide residue (L-nucleic acid catalyst). More specifically, the L-nucleic acid catalyst is an RNA or a DNA or combinations of ribo- and deoxyribo-nucleotides. Alternately, or in addition, the L-nucleic acid catalyst is modified at the base, sugar, and/or phosphate backbone individually or in combinations without entirely inhibiting the catalytic activity.

In another preferred embodiment the invention features a nucleic acid catalyst comprising at least two L-nucleotide substitutions of formula I, wherein said substitution is same or different.

In yet another preferred embodiment, the invention features a nucleic acid catalyst with L-nucleotide substitution of Formula I, wherein said nucleic acid can cleave a separate nucleic acid molecule, preferably a single-stranded nucleic acid, more specifically RNA.

In a preferred embodiment the invention features a nucleic acid catalyst with L-nucleotide substitution of Formula I, wherein the catalyst is in a hammerhead or a hairpin ribozyme motif.

In another aspect, the invention features a nucleic acid catalyst with L-nucleotide substitution of Formula I, wherein said nucleic acid ligates separate nucleic acid molecules.

The invention also features a nucleic acid molecule catalyst with L-nucleotide substitution of Formula I, wherein said nucleic acid molecule cleaves or forms amide or peptide linkages.

The term "nucleotide" is used as recognized in the art to include natural bases, and modified bases well known in the art. Such bases are generally located at the 1' position of a sugar moiety. Nucleotide generally comprise a base, sugar and a phosphate group. The nucleotides can be unmodified or modified at the sugar, phosphate and/or base moeity, (see for example, Usman and McSwiggen, supra; Eckstein et al., International PCT Publication No. WO 92/07065; Usman et al., International PCT Publication No. WO 93/15187; all hereby incorporated by reference herein). There are several examples of modified nucleic acid bases known in the art and has recently been summarized by Limbach et al., 1994, *Nucleic Acids Res.* 22, 2183. Some of the non-limiting examples of base modifications that can be introduced into enzymatic nucleic acids without significantly effecting their catalytic activity include, inosine, purine, pyridin-4-one, pyridin-2-one, phenyl, pseudouracil, 2,4,6-trimethoxy benzene, 3-methyluracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine) and others (Burgin et al., 1996, *Biochemistry,* 35, 14090). By "modified bases" in this aspect is meant nucleotide bases other than adenine, guanine, cytosine and uracil at 1' position or their equivalents; such bases may be used within the catalytic core of the enzyme and/or in the substrate-binding regions.

There are several examples in the art describing sugar modifications that can be introduced into enzymatic nucleic acid molecules without significantly effecting catalysis and significantly enhancing their nuclease stability and efficacy. Sugar modification of enzymatic nucleic acid molecules have been extensively described in the art (see Eckstein et al., *International Publication* PCT No. WO 92/07065; Perrault et al. *Nature* 1990, 344, 565–568; Pieken et al. *Science* 1991, 253, 314–317; Usman and Cedergren, *Trends in Biochem. Sci.* 1992, 17, 334–339; Usman et al. *International Publication* PCT No. WO 93/15187; Sproat, U.S. Pat. No. 5,334,711 and Beigelman et al., 1995 *J. Biol. Chem.* 270, 25702). Such publications describe the location of incorporation of modifications and the like, and are incorporated by reference herein. In view of such teachings, similar modifications can be used as described herein.

In a preferred embodiment the invention features a nucleic acid catalyst with non-nucleotide substitution. The non-nucleotide substituion are in addition to the L-nucleotide substitution and/or the non-nucleotide substitution is in the opposite enantiomeric form as the standard non-nucleotide residue. The term "non-nucleotide" as used herein include either abasic nucleotide, polyether, polyamine, polyamide, peptide, carbohydrate, lipid or polyhydrocarbon compounds. Specific examples include those described by Seela and Kaiser, *Nucleic Acids Res.* 1990, 18:6353 and Nucleic Acids Res. 1987, 15:3113; Cload and Schepartz, *J. Am. Chem. Soc.* 1991, 113:6324; Richardson and Schepartz, *J. Am. Chem. Soc.* 1991, 113:5109; Ma et al., *Nucleic Acids Res.* 1993, 21:2585 and *Biochemistry* 1993, 32:1751; Durand et al., *Nucleic Acids Res.* 1990, 18:6353; McCurdy et al., *Nucleosides & Nucleotides* 1991, 10:287; Jschke et al., *Tetrahedron Lett.* 1993, 34:301; Ono et al., *Biochemistry* 1991, 30:9914; Arnold et al., International Publication No. WO 89/02439; Usman et al., International Publication No. WO 95/06731; Dudycz et al., International Publication No. WO 95/11910 and Ferentz and Verdine, *J. Am. Chem. Soc.* 1991, 113:4000, all hereby incorporated by reference herein. Thus, in a preferred embodiment, the invention features an enzymatic nucleic acid molecule having one or more non-nucleotide moieties, and having enzymatic activity to cleave an RNA or DNA molecule. By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine. The term "abasic" or "abasic nucleotide" as used herein encompasses sugar moieties lacking a base or having other chemical groups in place of base at the 1' position.

In preferred embodiments, the enzymatic nucleic acid includes one or more stretches of RNA, which provide the enzymatic activity of the molecule, linked to the non-nucleotide moiety. The necessary RNA components are known in the art, se, e.g., Usman, supra. By RNA is meant a molecule comprising at least one ribonucleotide residue.

As the term is used in this application, non-nucleotide-containing enzymatic nucleic acid means a nucleic acid molecule that contains at least one non-nucleotide component which replaces a portion of a ribozyme, e.g., but not limited to, a double-stranded stem, a single-stranded "catalytic core" sequence, a single-stranded loop or a single-stranded recognition sequence. These molecules are able to cleave (preferably, repeatedly cleave) separate RNA or DNA molecules in a nucleotide base sequence specific manner. Such molecules can also act to cleave intramolecularly if that is desired. Such enzymatic molecules can be targeted to virtually any RNA transcript.

By "L-nucleotide" is meant a nucleotide having the opposite rotatory dispersion spectra to their naturally occurring D-enantiomers (Rosanoff, supra). Enantiomers as used herein is meant to indicate the mirror images of each other, as defined by Jacques et al., 1991, *Enantiomers, Racemates, and Resolutions,* pp 3, Krieger Publishing Co., Florida, U.S.A.

Jacques et al., 1991, *Enantiomers, Racemates, and Resolutions,* pp 3, Krieger Publishing Co., Florida, U.S.A., define chirality, racemates and enantiomers. They state on pages 3–4 that "Chirality is a concept well known to organic chemists and, indeed, to all chemists concerned in any way with structure. It has numerous implications ranging from those affecting physical properties of matter to those related to biological mechanisms. These implications extend far beyond the borders of "pure" chemistry.

The geometric property that is responsible for the non-identity of an object with its mirror image is called chirality. A chiral object may exist in two enantiomorphic forms which are mirror images of one another. Such forms lack inverse symmetry elements, that is, a center, a plane, and an improper axis of symmetry. Objects that possess one or more of these inverse symmetry elements are superposable on their mirror images; they are achiral. All objects necessarily belong to one of these categories; a hand, a spiral staircase, and a snail shell are all chiral, while a cube and a sphere are achiral.

All of the foregoing definitions remain valid at the molecular level; there are achiral as well as chiral molecules. The latter exist in two enantiomeric forms (the adjective enantiomorphic is more generally applied to macroscopic objects). The term enantiomer is used to designate either a single molecule, a homochiral collection of molecules, or even a heterochiral collection that contains an excess of one enantiomer and whose composition is defined by its enantiomeric purity p, or the enantiomeric excess e.e. which is equivalent to p.

The oldest known manifestation of molecular chirality is the optical activity, or rotatory power, the property that is exhibited by the rotation of the plane of polarization of light. The two enantiomers of a given compound have rotatory powers of equal absolute value but of opposite sign, or sense. One is positive, or dextrorotatory, while the other is negative, or levorotatory. The absolute designations of sign are arbitrary inasmuch as they are wavelength, temperature, and solvent dependent, but the relative designations are always valid. That is, a given enantiomer may be (+) at one wavelength and (−) at another. The other enantiomer will always have the opposite sign at the corresponding wavelength. While we shall use as often as possible the (+) and (−) symbols to designate a pair of enantiomers, we shall occasionally employ the letters d and l or D and L for convenience.

The absolute configuration of a chiral substance is known when an enantiomeric structure can be assigned to an optically active sample of a given sign. Recall that absolute configurations are designated by means of an alphabetic symbolism (R,S for rectus and sinister) whose application is determined by the rules of Cahn, Ingold, and Prelog. However, the D and L descriptors of Rosanoff are still used for carbohydrates. Care should be exercised so as not to confuse these with the sign of the optical activity." (emphasis added)

Tazawa et al., 1970, *Biochemistry,* 3499, described the synthesis of di-nucleotides with L-adenosine residues. They also reported that L-adenosine dimers are "completely" or "extremely" resistant to cleavage by spleen and snake venom phosphodiesterase enzymes.

Ashley, 1992, *J. Am. Chem. Soc.,* 114, 9731, RNA molecules composed entirely of L-ribonucleotides {(L)-RNA} can interact stably with a complementary (D)-RNA and poorly with a complementary (D)-DNA. He also mentions in the paper that (L)-RNA is "resistant to both purified ribonuclease A and total cell extracts of L-cells."

Klubmann et al., 1996, *Nature Biotech.,* 14, 1112; Nolte et al., 1996, *Nature Biotech.,* 14, 1116, describe a method of selecting L-oligonucleotide aptamers capable of binding D-adenosine and L-arginine ligands.

Schumacher and Kim, International PCT Publication No. WO 96/34879, describe a method of identifying "macromolecules (peptides, oligonucleotides, sugar and macromolecular complexes, such as RNA-protein complexes, protein-lipid complexes), which are not of the natural handedness (not of the chirality as they occur in nature or as wildtype molecule) and which are ligands for other chiral macromolecules." The publications cited above and elswhere in the application, describe general methods and strategies to determine the location of incorporation of sugar, base and/or phosphate modifications including the L-nucleotide substitution and the like into ribozymes without inhibiting catalysis, and are incorporated by reference herein. In view of such teachings, similar modifications can be used as described herein to modify the nucleic acid catalysts of the instant invention.

By the phrase "nucleic acid catalyst" is meant a nucleic acid molecule capable of catalyzing a variety of reactions including the ability to repeatedly cleave other separate nucleic acid molecules (endonuclease activity) in a nucleotide base sequence-specific manner. Such a molecule with endonuclease activity may have complementarity in a substrate binding region to a specified gene target, and also has an enzymatic activity that specifically cleaves RNA or DNA in that target. That is, the nucleic acid molecule with endonuclease activity is able to intramolecularly or intermolecularly cleave RNA or DNA and thereby inactivate a target RNA or DNA molecule. This complementarity functions to allow sufficient hybridization of the enzymatic RNA molecule to the target RNA or DNA to allow the cleavage to occur. 100% complementarity is preferred, but complementarity as low as 50–75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, nucleozyme, DNAzyme, RNA enzyme, endoribonuclease, endonuclease, minizyme, leadzyme, oligozyme or DNA enzyme. All of these terminologies describe nucleic acid molecules with enzymatic activity.

By "nucleic acid molecule" as used herein is meant a molecule comprising nucleotides. The nucleic acid can be composed of modified or unmodified nucleotides or non-nucleotides or various mixtures and combinations thereof.

By "complementarity" is meant a nucleic acid that can form hydrogen bond(s) with other RNA sequence by either traditional Watson-Crick or other non-traditional types (for example, Hoogsteen type) of base-paired interactions.

In preferred embodiments of this invention, the enzymatic nucleic acid molecule is formed in a hammerhead or hairpin motif, but may also be formed in the motif of a hepatitis delta virus (HDV), group I intron, RNaseP RNA (in association with an RNA guide sequence) or Neurospora VS RNA. Examples of such hammerhead motifs are described by Rossi et al., 1992, *Aids Research and Human Retroviruses* 8, 183, of hairpin motifs by Hampel et al., EP0360257, Hampel and Tritz, 1989 *Biochemistry* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849 and Forster and Altman, 1990 *Science* 249, 783, Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Guo and Collins, 1995 *EMBO J.* 14, 368) and of the Group I intron by Cech et al., U.S. Pat. No. 4,987,071. These specific motifs are not limiting in the invention and those skilled in the art will recognize that all that is important in an enzymatic nucleic acid molecule with endonuclease activity of this invention is that it has a specific substrate binding site which is complementary to one or more of the target gene RNA regions, and that it have nucleotide sequences within or surrounding that substrate binding site which impart an RNA cleaving activity to the molecule.

The invention provides a method for producing a class of enzymatic cleaving agents which exhibit a high degree of specificity for the target, such as RNA of a desired target. The enzymatic nucleic acid molecule is preferably targeted to a highly conserved sequence region of a target such that specific treatment of a disease or condition can be provided with a single enzymatic nucleic acid. Such enzymatic nucleic acid molecules can be delivered exogenously to specific cells as required. In the preferred hammerhead motif the small size (less than 60 nucleotides, preferably between 30–40 nucleotides in length) of the molecule allows the cost of treatment to be reduced compared to other ribozyme motifs.

Therapeutic ribozymes must remain stable within cells until translation of the target mRNA has been inhibited long enough to reduce the levels of the undesirable protein. This period of time varies between hours to days depending upon the disease state. Clearly, ribozymes must be resistant to nucleases in order to function as effective intracellular therapeutic agents. Improvements in the chemical synthesis of RNA (Wincott et al., 1995 *Nucleic Acids Res.* 23, 2677; incorporated by reference herein) have expanded the ability to modify ribozymes to enhance their nuclease stability. The majority of this work has been performed using hammerhead ribozymes (reviewed in Usman and McSwiggen, 1995 supra) and can be readily extended to other catalytic nucleic acid motifs.

By "enzymatic portion" is meant that part of the ribozyme essential for cleavage of an RNA substrate.

By "substrate binding arm" is meant that portion of a ribozyme which is complementary to (i.e., able to base-pair with) a portion of its substrate. Generally, such complementarity is 100%, but can be less if desired. For example, as few as 10 bases out of 14 may be base-paired. Such arms are shown generally in FIG. 1 as discussed below. That is, these arms contain sequences within a ribozyme which are intended to bring ribozyme and target RNA together through complementary base-pairing interactions; e.g., ribozyme sequences within stems I and III of a standard hammerhead ribozyme make up the substrate-binding domain (see FIG. 1).

In a preferred embodiment, the enzymatic nucleic acid molecules are added directly, or can be complexed with cationic lipids, packaged within liposomes, or otherwise delivered to smooth muscle cells. The RNA or RNA complexes can be locally administered to relevant tissues through the use of a catheter, infusion pump or stent, with or without their incorporation in biopolymers. Using the methods described herein, other enzymatic nucleic acid molecules that cleave target nucleic acid may be derived and used as described above. Specific examples of nucleic acid catalysts of the instant invention are provided below in the Tables and figures.

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., supra which have been incorporated by reference herein.

By "consists essentially of" is meant that the active ribozyme contains an enzymatic center or core equivalent to those in the examples, and binding arms able to bind target nucleic acid molecules such that cleavage at the target site occurs. Other sequences may be present which do not interfere with such cleavage.

Thus, in one aspect, the invention features ribozymes that inhibit gene expression and/or cell proliferation. These chemically or enzymatically synthesized nucleic acid molecules contain substrate binding domains that bind to accessible regions of specific target nucleic acid molecules. The nucleic acid molecules also contain domains that catalyze the cleavage of target. Upon binding, the enzymatic nucleic acid molecules cleave the target molecules, preventing for example, translation and protein accumulation. In the absence of the expression of the target gene, cell proliferation, for example, is inhibited.

By "patient" is meant an organism which is a donor or recipient of explanted cells or the cells themselves. "Patient" also refers to an organism to which enzymatic nucleic acid molecules can be administered. Preferably, a patient is a mammal or mammalian cells. More preferably, a patient is a human or human cells.

In a preferred embodiment, the invention features a method of synthesis of enzymatic nucleic acid molecules of instant invention which follows the procedure for normal chemical synthesis of RNA as described in Usman et al., 1987 *J. Am. Chem. Soc.,* 109, 7845; Scaringe et al., 1990 *Nucleic Acids Res.,* 18, 5433; and Wincott et al., 1995 *Nucleic Acids Res.* 23, 2677–2684 and makes use of common nucleic acid protecting and coupling groups, such as dimethoxytrityl at the 5'-end, and phosphoramidites at the 3'-end. Small scale synthesis were conducted on a 394 Applied Biosystems, Inc. synthesizer using a modified 2.5 μmol scale protocol with a 5 min coupling step for alkylsilyl protected nucleotides and 2.5 min coupling step for 2'-O-methylated nucleotides. Table II outlines the amounts, and the contact times, of the reagents used in the synthesis cycle. A 6.5-fold excess (163 μL of 0.1 M=16.3 μmol) of phosphoramidite and a 24-fold excess of S-ethyl tetrazole (238 μL of 0.25 M=59.5 μmol) relative to polymer-bound 5'-hydroxyl is used in each coupling cycle. Average coupling yields on the 394 Applied Biosystems, Inc. synthesizer, determined by calorimetric quantitation of the trityl fractions, is 97.5–99%. Other oligonucleotide synthesis reagents for the 394 Applied Biosystems, Inc. synthesizer: detritylation solution was 2% TCA in methylene chloride (ABI); capping was performed with 16% N-methyl imidazole in THF (ABI) and 10% acetic anhydride/10% 2,6-lutidine in THF (ABI); oxidation solution was 16.9 mM $I_2$, 49 mM pyridine, 9% water in THF (Millipore). B & J Synthesis Grade acetonitrile is used directly from the reagent bottle. S-Ethyl tetrazole solution (0.25 M in acetonitrile) is made up from the solid obtained from American International Chemical, Inc.

In a preferred embodiment, deprotection of the chemically synthesized nucleic acid catalysts of the invention is performed as follows. The polymer-bound oligoribonucleotide, trityl-off, is transferred from the synthesis column to a 4 mL glass screw top vial and suspended in a solution of methylamine (MA) at 65° C. for min. After cooling to −20° C., the supernatant is removed from the polymer support. The support is washed three times with 1.0 mL of EtOH:MeCN:$H_2O$/3:1:1, vortexed and the supernatant is then added to the first supernatant. The combined supernatants, containing the oligoribonucleotide, are dried to a white powder.

The base-deprotected oligoribonucleotide is resuspended in anhydrous TEA.HF/NMP solution (250 μL of a solution of 1.5 mL N-methylpyrrolidinone, 750 μL TEA and 1.0 mL TEA.3HF to provide a 1.4M HF concentration) and heated to 65° C. for 1.5 h. The resulting, fully deprotected, oligomer is quenched with 50 mM TEAB (9 mL) prior to anion exchange desalting.

For anion exchange desalting of the deprotected oligomer, the TEAB solution is loaded on to a Qiagen 500® anion exchange cartridge (Qiagen Inc.) that is prewashed with 50 mM TEAB (10 mL). After washing the loaded cartridge with 50 mM TEAB (10 mL), the RNA is eluted with 2 M TEAB (10 mL) and dried down to a white powder. The average stepwise coupling yields are generally >98% (Wincott et al., 1995 *Nucleic Acids Res.* 23, 2677–2684).

In a preferred embodiment, the ribozymes of the instant invention are also synthesized from DNA templates using bacteriophage T7 RNA polymerase (Milligan and Uhlenbeck, 1989, *Methods Enzymol.* 180, 51).

In another embodiment, the ribozymes are purified by gel electrophoresis using general methods or are purified by high pressure liquid chromatography (HPLC; See Wincott et al., supra) the totality of which is hereby incorporated herein by reference) and are resuspended in water.

In a preferred embodiment, in addition to L-nucleotide substitution, the nucleic acid catalysts of the invention are modified to enhance stability and/or enhance catalytic activity by modification with nuclease resistant groups, for example, 2'-amino, 2'-C-allyl, 2'-flouro, 2'-O-methyl, 2'-H, nucleotide base modifications (for a review see Usman and Cedergren, 1992 *TIBS* 17, 34; Usman et al., 1994 *Nucleic Acids Symp. Ser.* 31, 163; Burgin et al., 1996 *Biochemistry* 35, 14090).

In a preferred embodiment the molecules of the invention are purified by gel electrophoresis using general methods or are purified by high pressure liquid chromatography (HPLC; See Wincott et al., supra) the totality of which is hereby incorporated herein by reference) and are resuspended in water.

In another preferred embodiment, catalytic activity of the molecules described in the instant invention can be optimized as described by Draper et al., supra. The details will not be repeated here, but include altering the length of the ribozyme binding arms, or chemically synthesizing ribozymes with modifications (base, sugar and/or phosphate) that prevent their degradation by serum ribonucleases and/or enhance their enzymatic activity (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162; Sproat, U.S. Pat. No. 5,334, 711; and Burgin et al., supra; all of these describe various chemical modifications that can be made to the base, phosphate and/or sugar moieties of enzymatic RNA molecules). Modifications which enhance their efficacy in cells, and removal of bases from stem loop structures to shorten RNA synthesis times and reduce chemical requirements are desired. (All these publications are hereby incorporated by reference herein.).

By "enhanced enzymatic activity" is meant to include activity measured in cells and/or in vivo where the activity is a reflection of both catalytic activity and ribozyme stability. In this invention, the product of these properties is increased or not significantly (less that 10 fold) decreased in vivo compared to an all RNA ribozyme.

In yet another preferred embodiment, nucleic acid catalysts having chemical modifications which maintain or enhance enzymatic activity is provided. Such nucleic acid is also generally more resistant to nucleases than unmodified nucleic acid. Thus, in a cell and/or in vivo the activity may not be significantly lowered. As exemplified herein such ribozymes are useful in a cell and/or in vivo even if activity over all is reduced 10 fold (Burgin et al., 1996, *Biochemistry*, 35, 14090). Such ribozymes herein are said to "maintain" the enzymatic activity on all RNA ribozyme.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1 is a diagrammatic representation of the hammerhead ribozyme domain known in the art. Stem II can be ≧2 base-pair long. Each N is independently any base or non-nucleotide as used herein.

FIG. 2a is a diagrammatic representation of the hammerhead ribozyme domain known in the art;

FIG. 2b is a diagrammatic representation of the hammerhead ribozyme as divided by Uhlenbeck (1987, *Nature*, 327, 596–600) into a substrate and enzyme portion;

FIG. 2c is a similar diagram showing the hammerhead divided by Haseloff and Gerlach (1988, *Nature*, 334, 585–591) into two portions; and FIG. 2d is a similar diagram showing the hammerhead divided by Jeffries and Symons (1989, *Nucl. Acids. Res.*, 17, 1371–1371) into two portions.

FIG. 3 is a diagrammatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is ≧1 base). Helix 1, 4 or may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is ≧2 bases. The connecting loop can also be replaced with a non-nucleotide linker molecule. H refers to bases A, U, or C. Y refers to pyrimidine bases. "_" refers to a covalent bond.

FIG. 4 is a representation of the general structure of the hepatitis delta virus ribozyme domain known in the art. In each instance, each N and N' independently is any normal or modified base and each dash represents a potential base-pairing interaction. These nucleotides may be modified at the sugar, base or phosphate.

FIG. 5 is a representation of the general structure of the self-cleaving VS RNA ribozyme domain.

FIG. 6 shows the general structure of a D-nucleotide and a L-nucleotide.

FIG. 7 shows a scheme for the phosphoramidite synthesis of L-ribonucleosides (Scheme 1).

FIG. 8 shows a scheme for the phosphoramidite synthesis of L-ribonucleosides using 5'-O-silyl protection (Scheme 2).

FIG. 9 shows A) a scheme for the synthesis of L-2'-amino-2'-deoxy-pyrimidine phosphoramidites. B) a scheme for the synthesis of L-2'-amino-2'-deoxy-purine phosphoramidites.

FIG. 10 is a diagrammatic representation of a hammerhead ribozyme-substituted with L-nucleotides.

FIG. 11 is a graphical representation of RNA cleavage reaction catalyzed by hammerhead ribozymes with L-nucleotide substitutions.

NUCLEOTIDES AND NUCLEOSIDES

Applicant has found that chemical modifications of this invention are particulary useful for enzymatic nucleic acid molecule stabilization. Thus, below is provided examples of one such molecule, a hammerhead ribozyme. Those in the art will recognize that equivalent procedures can be used to make other enzymatic nucleic acid molecules having L-nucleotide substitution. Specifically, FIG. 1 shows base numbering of a hammerhead motif in which the numbering of various nucleotides in a hammerhead ribozyme is provided. This is not to be taken as an indication that the Figure is prior art to the pending claims, or that the art discussed is prior art to those claims.

EXAMPLES

The following are non-limiting examples showing the synthesis and activity of nucleic acid catalysts containing L-nucleotide substitutions and the synthesis of monomer phosphoramidites.

Example 1: Synthesis of enzymatic nucleic acids comprising L-nucleotide substitutions The method of synthesis follows the procedure for normal RNA synthesis as described in Usman et al., *J. Am. Chem. Soc.* 1987, 109, 7845–7854; Scaringe et al., *Nucleic Acids Res.* 1990, 18, 5433–5441; and Wincott et al., 1995, *Nucleic Acids Res.* 23, 2677 (all of these references are incorporated by reference herein in their entirety) and makes use of common nucleic acid protecting and coupling groups, such as dimethoxytrityl at the 5'-OH, and phosphoramidites at the 3'-OH. Phosphoramidites of L-nucleosides may be incorporated not only into hammerhead ribozymes, but also into hairpin, hepatitis delta virus, VS RNA, RNase P ribozyme, Group I, Group II intron or other catalytic nucleic acids. They are, therefore, of general use in any catalytic nucleic acid structure.

Example 2: Phosphoramidite synthesis of L-ribonucleosides (Scheme 1)

Referring to FIG. 7, L-ribose was converted to 1-O-methyl-α, β-L-ribofuranoside by action of HCl/MeOH as described (Visser et al., *Recl. Trav. Pays-Bas* 1986, 105, 528–537). This intermediate was further benzoylated by BzCl/py and the resulting 1-O-methyl-2,3,5-tri-O-benzoyl-L-ribofuranoside was subjected to the acetolysis procedure (Ac2O/AcOH/$H_2SO_4$). The target 1-O-acetyl-2,3,5-tri-O-benzoyl-β-L-ribofuranoside was isolated in ~30k yield from L-Ribose and served as a starting material for the synthesis of L-ribonucleosides in 50–75i yield by Vorbruggen procedure (Vorbruggen et al., 1981, *Chem. Ber.* 114, 1234).

The ribose portion of the fully protected ribonucleosides were deprotected by NaOMe/MeOH treatment (Urd) and NaOH/dioxane (Cbz, Abz, Gibu). Subsequently, standard tritylation, silylation, separation of the 2' and 3'-O-TBDMSi isomers and phospitylation procedures yielded target phosphoramidites.

The phosphoramidites were incorporated into hammerhead ribozymes using general procedures for RNA synthesis and deprotection which have been described previously (Wincott et al., supra, incorporated by reference herein in its entirety). Synthesis was carried out on a 394 (ABI) synthesizer using a modified 2.5 μmol scale protocol with a 5 min coupling step for 2'-O-TBDMSi protected nucleotides and 2.5 min coupling step for 2'-O-methyl nucleotides. A 6.5-fold excess of a 0.1 M solution phosphoramidite and a 24-fold excess of S-ethyl tetrazole relative to polymer-bound 5'-hydroxyl was used in each coupling cycle.

All analytical HPLC analyses were performed on a Hewlett Packard 1090 HPLC with a Dionex NucleoPac® PA-100 column, 4×250 mm, at 50° C., as reported (Wincott et al., supra).

CGE analyses were performed on a Hewlett Packard $^{3D}$CE with a J & W μPAGE™-5 (5% T, 5% C) polyacrylamide gel-filled column, 75 μm I.D.×75 cm, 50 cm effective length, 100 mM Tris-Borate, 7 M Urea, pH=8.3, and J & W μPAGE™ Buffer (100 mM Tris-Borate, 7 M Urea, pH=8.3). Samples were electrokinetically injected using −13 kV for 3–10 sec, run at −13 kV and detected at 260 nm.

MALDI-TOF mass spectra were determined on a PerSeptive Biosystems Voyager spectrometer.

Example 3: Phosphoramidite synthesis of L-ribonucleosides (Scheme 2)

The above standard Scheme 1 has been used extensively (Klubmann et al., supra and Ashley, Supra) and has certain disadvantages; a) L-Ribose Is expensive and the yield of the key intermediate 1-O-acetyl-2,3,5-tri-O-benzoyl-β-L-ribofuranoside, necessary for synthesis of L-ribonucleosides is low (~30%); b) conversion to the N-protected 5'-O-DMT derivatives is not very efficient (typical yield is 40–50%) because of difficulties in the selective removal of ribose protecting groups without effecting base protection and tedious isolation of resulting intermediates to be used in tritylation reaction.

These problems can be overcome by introduction of orthogonal protection for the 5-O-group during the first step of the synthesis (see FIG. 8). This serves two purposes: 1) effective conversion of L-Ribose to the 5-O-tret-bytuldiphenylsilyl-1,2,3-O-benzoyl ribofuranose which serves as a precursor for glycosilation is achieved (60% vs 30% in Scheme 1); 2) Orthogonality of 5'-O-TBDPSi group to the acyl type ribose and base protection in fully blocked L-ribonucleosides allows selective removal of this group with effective isolation of 5'-OH intermediate and subsequent efficient 5'-tritylation. Removal of 2',3'-protecting groups from 5'-O-DMT intermediates and isolation of the target 5'-O-DMT-N-protected L-ribonucleosides is much more efficient due to lipohilicity of 5'-O-DMT group.

Example 4: Synthesis of L-2'-amino-2'-deoxy-uridine and pyrimidine phosphoramidite Referring to FIG. 9A, L-Arabinose was converted to the 2,2'-Anhydro-L-uridine (2) through 2-Amino-β-L-arabinofurano[1',2':4,5]oxazoline (1) according to the procedure of Holy, *Coll. Czech. Chem. Commun.* 1972 4072–4087. The opening of 2,2' anhydro ring with lithium azide and subsequent reduction to 2'-amino-uridine 4 was performed as described (Verheyden et al., *J. Org Chem.* 1971, 36,250–254; Hobbs et al., *J. Org. Chem.* 1979, 42, 714–719). The conversion of nucleoside (4) to the target phosphoramidite (6) was accomplished according to Beigelman et al., *Nucleic Acids Res.,* 1995, 4434–4442.

The key intermediate 4 was also converted to 2'-deoxy-2'-azido-cytidine by standard transformation according to Divakar et al., 1982, *J. Chem. Soc. Perkin I,* 1171, protected at N4 by benzoyl group, tritylated and the 2'-N3 function reduced to 2'-amino as in the case of uridine. Above intermediate was further transformed into phosphoramidite using the same procedures for the incorporation of phthaloyl protection and phosphitylation as for Uridine.

Example 5: Synthesis of L-2'-amino-2'-deoxy-purine phosphoramidite

Referring to FIG. 9B, L-ribonucleosides of A and G, were obtained from L-ribose as shown in Scheme 1 and 2 above. They were N-protected using transient protection method (Ti et al., *JACS* 1982, 104, 1316–19) and then 3'- and 5'-protected by Markiewich protecting group. The resulting intermediates 1 were oxidized by $CrO_3$/Py and the resulting 2-keto compounds were reduced to the 2'-xylo derivatives 2. Subsequent tritylation and nucleophilic displacement with $LiN_3$ according to Robins et al., (*Nucleosides & Nucleotides* 1992 11, 821–834) resulted in 2'-N3-derivatives 3. The azido group in 3 was reduced with $Ph_3P/NH_4OH$ followed by desilylation. The resulting 2'-amino nucleoside 4 was isolated in ~60% yield. Transformation of intermediates 4 into phosphoramidites 6 was accomplished analogously to related pyrimidne derivatives according to Beigelman et al., supra.

Example 6: Catalytic activity of L-nucleotide-substituted ribozymes

Hammerhead ribozymes were substituted with L-nucleotides at several positions (FIG. 10). The relative effect of L-nucleotide-substitution on ribozyme catalytic activity was investigated under standard assay conditions as described, supra, in Materials and Methods.

RNA Cleavage Assay In Vitro

Substrate RNA is 5' end-labeled using [γ-$^{32}$P] ATP and T4 polynucleotide kinase (U.S. Biochemicals) Cleavage reactions are carried out under ribozyme "excess" conditions. Trace amount (≦1 nM) of 5' end-labeled substrate and 40 nM unlabeled ribozyme are denatured and renatured separately by heating to 90° C. for 2 min and snap-cooling on ice for 10–15 min. The ribozyme and substrate are incubated, separately, at 37° C. for 10 min in a buffer containing 50 mM Tris-HCl and 10 mM $MgCl_2$. The reaction is initiated by mixing the ribozyme and substrate solutions and incubating at 37° C. Aliquots of 5 μl are taken at regular intervals of time and the reaction is quenched by mixing with equal volume of 2×formamide stop mix. The samples are resolved on 20% denaturing polyacrylamide gels. The results are quantified and percentage of target RNA cleaved is plotted as a function of time.

Referring to FIG. 11, hammerhead ribozymes with L-nucleotide substitution at one or more positions were all catalytically active to cleave target RNA.

Sequence of ribozymes, target sequence, ribozyme motif and positions of L-nucleotide substitution described in the above and in this specification are meant to be non-limiting examples, and those skilled in the art will recognize that other nucleic acid catalytic motifs, sequences of target and L-nucleotide substitutions (base, sugar and phosphate modifications) can be readily generated using standard techniques and are hence within the scope of this invention.

Example 7: In vitro selection of L-nucleic acid catalysts

In vitro selection (evolution) strategies (orgel, 1979, *Proc. R. Soc. London,* B 205, 435) can be used to evolve L-nucleotide comprising nucleic acid catalysts capable of catalyzing a variety of reactions, such as cleavage and ligation of phosphodiester linkages and amide linkages. Any one of a number of different approaches to carry out in vitro selection that have been described and reviewed (Joyce, 1989, *Gene,* 82, 83–87; Beaudry et al.,1992, *Science* 257, 635–641; Joyce, 1992, *Scientific American* 267, 90–97; Breaker et al., 1994, *TIBTECH* 12, 268; Bartel et al., 1993, *Science* 261:1411–1418; Szostak, 1993, *TIBS* 17, 89–93; Kumar et al., 1995, *FASEB J.,* 9, 1183; Breaker, 1996, *Curr. Op. Biotech.,* 7, 442; Schumacher et al., 1996, supra; Nolte et al., 1996, supra; Klubmann et al., 1996, supra; Breaker, 1997, *Chem. Rev.,* in Press) and any other related approach can be used to evolve and/or select L-nucleotide comprising nucleic acid catalyst and are within the scope of the invention.

Ribozyme Engineering

Sequence, chemical and structural variants nucleic acid catalysts can be engineered using the techniques shown above and known in the art to cleave a separate target RNA or DNA in trans (Zaug et al., 1986, *Nature,* 324, 429; Ruffner et al., 1990, *Biochem.,* 29, 10695; Beaudry et al., 1990, *Biochem.,* 29, 6534; McCall et al., 1992, *Proc. Natl. Acad. Sci., USA,* 89, 5710; Long et al., 1994, Supra; Hendry et al., 1994, *BBA* 1219, 405; Benseler et al., 1993, *JACS,* 115, 8483; Thompson et al., 1996, *Nucl. Acids Res.,* 24, 4401;Michels et al., 1995, *Biochem.,* 34, 2965; Been et al., 1992, *Biochem.,* 31, 11843; Guo et al., 1995, *EMBO. J.,* 14, 368; Pan et al., 1994, *Biochem.,* 33, 9561; Cech, 1992, *Curr. Op. Struc. Bio.,* 2, 605; Sugiyama et al., 1996, *FEBS Lett.,* 392, 215; Beigelman et al., 1994, *Bioorg. Med. Chem.,* 4, 1715; all are incorporated in its totality by reference herein).

Diagnostic Uses

Enzymatic nucleic acids of this invention may be used as diagnostic tools to examine genetic drift and mutations within diseased cells or to detect the presence of target RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with disease condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Additional Uses

Nucleic acid molecules of the instant invention might have many of the same applications for the study of RNA that DNA restriction endonucleases have for the study of DNA (Nathans et al., 1975 *Ann. Rev. Biochem.* 44:273). For example, the pattern of restriction fragments could be used to establish sequence relationships between two related RNAs, and large RNAs could be specifically cleaved to fragments of a size more useful for study. The ability to engineer sequence specificity of the ribozyme is ideal for cleavage of RNAs of unknown sequence.

SEQUENCE LISTING

<160> NUMBER OF SEQ ID NOS: 11

<210> SEQ ID NO 1
<211> LENGTH: 11
<212> TYPE: RNA

```
<213> ORGANISM: Unidentified
<220> FEATURE:
<223> OTHER INFORMATION: n can be any base
<223> OTHER INFORMATION: Cleavage occurs between base in position
      5 and 6
<223> OTHER INFORMATION: h, in position 6, can be a, c or u

<400> SEQUENCE: 1
nnnnuhnnnn n                                                               11

<210> SEQ ID NO 2
<211> LENGTH: 28
<212> TYPE: RNA
<213> ORGANISM: Unidentified
<220> FEATURE:
<223> OTHER INFORMATION: Hammerhead Ribozyme
<223> OTHER INFORMATION: n, in position 1-5, 10, 14-19 and 25-28, can be any base

<400> SEQUENCE: 2
nnnnncugan gagnnnnnnc gaaannnn                                             28

<210> SEQ ID NO 3
<211> LENGTH: 15
<212> TYPE: RNA
<213> ORGANISM: Unidentified
<220> FEATURE:
<223> OTHER INFORMATION: Substrate for Hairpin Ribozyme
<223> OTHER INFORMATION: y, in position 12, can be c or u
<223> OTHER INFORMATION: h, in position 11, can be a, c or u
<223> OTHER INFORMATION: n, in position 1-7, 9 and 13-15, can be any
      base

<400> SEQUENCE: 3
nnnnnnnyng hynnn                                                           15

<210> SEQ ID NO 4
<211> LENGTH: 47
<212> TYPE: RNA
<213> ORGANISM: Unidentified
<220> FEATURE:
<223> OTHER INFORMATION: Hairpin Ribozyme
<223> OTHER INFORMATION: h, in position 23, can be a, c or u
<223> OTHER INFORMATION: n, in position 1-4, 9-19, 25-31 and 39-47,
      can be any base

<400> SEQUENCE: 4
nnnngaagnn nnnnnnnna aahannnnnn nacauuacnn nnnnnnn                         47

<210> SEQ ID NO 5
<211> LENGTH: 48
<212> TYPE: RNA
<213> ORGANISM: Hepatitis Delta Virus (HDV)
<220> FEATURE:
<223> OTHER INFORMATION: HDV Ribozyme
<223> OTHER INFORMATION: n, in position 17-23, can be any base

<400> SEQUENCE: 5
cuccaccucc ugcggunnnn nnngggcuac uucgguaggc uaagggag                       48

<210> SEQ ID NO 6
<211> LENGTH: 176
<212> TYPE: RNA
<213> ORGANISM: Neurospora VS
<220> FEATURE:
<223> OTHER INFORMATION: Neurospora VS Ribozyme

<400> SEQUENCE: 6
gggaaagcuu gcgaagggcg ucgucgcccc gagcgguagu aagcagggaa cucaccucca          60
```

```
auuucaguac ugaaauuguc guagcaguug acuacuguua ugugauuggu agaggcuaag      120
ugacgguauu ggcguaaguc aguauugcag cacagcacaa gcccgcuugc gagaau          176
```

<210> SEQ ID NO 7
<211> LENGTH: 15
<212> TYPE: RNA
<213> ORGANISM: Unidentified
<220> FEATURE:
<223> OTHER INFORMATION: Substrate RNA

<400> SEQUENCE: 7

```
agggauuaau ggaga                                                       15
```

<210> SEQ ID NO 8
<211> LENGTH: 36
<212> TYPE: RNA
<213> ORGANISM: Unidentified
<220> FEATURE:
<223> OTHER INFORMATION: Hammerhead Ribozyme
<223> OTHER INFORMATION: n, in position 11, is L-Uridine

<400> SEQUENCE: 8

```
ucuccaucug angaggccga aaggccgaaa aucccu                                36
```

<210> SEQ ID NO 9
<211> LENGTH: 36
<212> TYPE: RNA
<213> ORGANISM: Unidentified
<220> FEATURE:
<223> OTHER INFORMATION: Hammerhead Ribozyme
<223> OTHER INFORMATION: n, in position 9, is L-Uridine

<400> SEQUENCE: 9

```
ucuccaucng augaggccga aaggccgaaa aucccu                                36
```

<210> SEQ ID NO 10
<211> LENGTH: 36
<212> TYPE: RNA
<213> ORGANISM: Unidentified
<220> FEATURE:
<223> OTHER INFORMATION: Hammerhead Ribozyme
<223> OTHER INFORMATION: n, in position 36, is L-Uridine

<400> SEQUENCE: 10

```
ucuccaucug augaggccga aaggccgaaa aucccn                                36
```

<210> SEQ ID NO 11
<211> LENGTH: 36
<212> TYPE: RNA
<213> ORGANISM: Unidentified
<220> FEATURE:
<223> OTHER INFORMATION: Hammerhead Ribozyme
<223> OTHER INFORMATION: n, in position 9 and 11, is L-Uridine

<400> SEQUENCE: 11

```
ucuccaucng angaggccga aaggccgaaa aucccu                                36
```

TABLE 1

Characteristics of naturally occurring ribozymes

Group I Introns

- Size: ~150 to >1000 nucleotides.

TABLE 1-continued

Characteristics of naturally occurring ribozymes

- Requires a U in the target sequence immediately 5' of the cleavage site.
- Binds 4–6 nucleotides at the 5'-side of the cleavage site.
- Reaction mechanism: attack by the 3'-OH of guanosine to generate cleavage products with 3'-OH and 5'-guanosine.
- Additional protein cofactors required in some cases to help folding and maintenance of the active structure [1].
- Over 300 known members of this class. Found as an intervening sequence in *Tetrahymena thermophila* rRNA, fungal mitochondria, chloroplasts, phage T4, blue-green algae, and. others.
- Major structural features largely established through phylogenetic comparisons, mutagenesis, and biochemical studies [2,3].
- Complete kinetic framework established for one ribozyme [4,5,6,7].
- Studies of ribozyme folding and substrate docking underway [8,9,10].
- Chemical modification investigation of important residues well established [11,12].
- The small (4–6 nt) binding site may make this ribozyme too non-specific for targeted RNA cleavage, however, the Tetrahymena group I intron has been used to repair a "defective" β-galactosidase message by the ligation of new β-galactosidase sequences onto the defective message [13].

RNAse P RNA (M1 RNA)

- Size: ~290 to 400 nucleotides.
- RNA portion of a ubiquitous ribonucleoprotein enzyme.
- Cleaves tRNA precursors to form mature tRNA [14].
- Reaction mechanism: possible attack by $M^{2+}$-OH to generate cleavage products with 3'-OH and 5'-phosphate.
- RNAse P is found throughout the prokaryotes and eukaryotes. The RNA subunit has been sequenced from bacteria, yeast, rodents, and primates.
- Recruitment of endogenous RNAse P for therapeutic applications is possible through hybridization of an External Guide Sequence (EGS) to the target RNA [15,16]
- Important phosphate and 2' OH contacts recently identified [17,18]

Group II Introns

- Size: >1000 nucleotides.
- Trans cleavage of target RNAs recently demonstrated [19,20].
- Sequence requirements not fully determined.
- Reaction-mechanism: 2'-OH of an internal adenosine generates cleavage products with 3'-OH and a "lariat" RNA containing a 3'-5' and a 2'-5' branch point.
- Only natural ribozyme with demonstrated participation in DNA cleavage [21,22] in addition to RNA cleavage and ligation.
- Major structural features largely established through phylogenetic comparisons [23].
- Important 2' OH contacts beginning to be identified [24]
- Kinetic framework under development [25]

Neurospora VS RNA

- Size: ~144 nucleotides.
- Trans cleavage of hairpin target RNAs recently demonstrated [26].
- Sequence requirements not fully determined.
- Reaction mechanism: attack by 2'-OH 5' to the scissile bond to generate cleavage products with 2',3'-cyclic phosphate and 5'-OH ends.
- Binding sites and structural requirements not fully determined.
- Only 1 known member of this class. Found in Neurospora VS RNA.

Hammerhead Ribozyme
(see text for references)

- Size: ~13 to 40 nucleotides.
- Requires the target sequence UH immediately 5' of the cleavage site.
- Binds a variable number nucleotides on both sides of the cleavage site.
- Reaction mechanism: attack by 2'-OH 5' to the scissile bond to generate cleavage products with 2',3'-cyclic phosphate and 5'-OH ends.
- 14 known members of this class. Found in a number of plant pathogens (virusoids) that use RNA as the infectious agent.
- Essential structural features largely defined, including 2 crystal structures []
- Minimal ligation activity demonstrated (for engineering through in vitro selection) []
- Complete kinetic framework established for two or more ribozymes [].
- Chemical modification investigation of important residues well established [].

Hairpin Ribozyme

- Size: ~50 nucleotides.
- Requires the target sequence GUC immediately 3' of the cleavage site.
- Binds 4–6 nucleotides at the 5'-side of the cleavage site and a variable number to the 3'-side of the cleavage site.
- Reaction mechanism: attack by 2'-OH 5' to the scissile bond to generate cleavage products with 2',3'-cyclic phosphate and 5'-OH ends.
- 3 known members of this class. Found in three plant pathogen (satellite RNAs of the tobacco ringspot virus, arabis mosaic virus and chicory yellow mottle virus) which uses RNA as the infectious agent.
  Essential structural features largely defined [27,28,29,30]

TABLE 1-continued

Characteristics of naturally occurring ribozymes

- Ligation activity (in addition to cleavage activity) makes ribozyme amenable to engineering through in vitro selection [31]
- Complete kinetic framework established for one ribozyme [32].
- Chemical modification investigation of important residues begun [33,34].

Hepatitis Delta Virus (HDV) Ribozyme

- Size: ~60 nucleotides.
- Trans cleavage of target RNAs demonstrated [35].
- Binding sites and structural requirements not fully determined, although no sequences 5' of cleavage site are required. Folded ribozyme contains a pseudoknot structure [36].
- Reaction mechanism: attack by 2'-OH 5' to the scissile bond to generate cleavage products with 2',3'-cyclic phosphate and 5'-OH ends.
- Only 2 known members of this class. Found in human HDV.
- Circular form of HDV is active and shows increased nuclease stability [37]

---

1. Mohr, G.; Caprara, M. G.; Guo, Q.; Lambowitz, A. M. Nature, 370, 147–150 (1994).
2. Michel, Francois; Westhof, Eric. Slippery substrates. Nat. Struct. Biol. (1994), 1(1), 5–7.
3. Lisacek, Frederique; Diaz, Yolande; Michel, Francois. Automatic identification of group I intron cores in genomic DNA sequences. J. Mol. Biol. (1994), 235(4), 1206–17.
4. Herschlag, Daniel; Cech, Thomas R.. Catalysis of RNA cleavage by the Tetrahymena thermophila ribozyme. 1. Kinetic description of the reaction of an RNA substrate complementary to the active site. Biochemistry (1990), 29(44), 10159–71.
5. Herschlag, Daniel; Cech, Thomas R.. Catalysis of RNA cleavage by the Tetrahymena thermophila ribozyme. 2. Kinetic description of the reaction of an RNA substrate that forms a mismatch at the active site. Biochemistry (1990), 29(44), 10172–80.
6. Knitt, Deborah S.; Herschlag, Daniel. pH Dependencies of the Tetrahymena Ribozyme Reveal an Unconventional Origin of an Apparent pKa. Biochemistry (1996), 35(5), 1560–70.
7. Bevilacqua, Philip C.; Sugimoto, Naoki; Turner, Douglas H.. A mechanistic framework for the second step of splicing catalyzed by the Tetrahymena ribozyme. Biochemistry (1996), 35(2), 648–58.
8. Li, Yi; Bevilacqua, Philip C.; Mathews, David; Turner, Douglas H.. Thermodynamic and activation parameters for binding of a pyrene-labeled substrate by the Tetrahymena ribozyme: docking is not diffusion-controlled and is driven by a favorable entropy change. Biochemistry (1995), 34(44), 14394–9.
9. Banerjee, Aloke Raj; Turner, Douglas H.. The time dependence of chemical modification reveals slow steps in the folding of a group I ribozyme. Biochemistry (1995), 34(19), 6504–12.
10. Zarrinkar, Patrick P.; Williamson, James R.. The P9.1–P9.2 peripheral extension helps guide folding of the Tetrahymena ribozyme. Nucleic Acids Res. (1996), 24(5), 854–8.
11. Strobel, Scott A.; Cech, Thomas R.. Minor groove recognition of the conserved G.cntdot.U pair at the Tetrahymena ribozyme reaction site. Science (Washington, D.C.) (1995), 267(5198), 675–9.
12. Strobel, Scott A.; Cech, Thomas R.. Exocyclic Amine of the Conserved G.cntdot.U Pair at the Cleavage Site of the Tetrahymena Ribozyme Contributes to 5'-Splice Site Selection and Transition State Stabilization. Biochemistry (1996), 35(4), 1201–11.
13. Sullenger, Bruce A.; Cech, Thomas R.. Ribozyme-mediated repair of defective mRNA by targeted trans-splicing. Nature (London) (1994), 371(6498), 619–22.
14. Robertson, H.D.; Altman, S.; Smith, J.D. J. Biol. Chem., 247 5243–5251 (1972).
15. Forster, Anthony C.; Altman, Sidney. External guide sequences for an RNA enzyme. Science (Washington, D.C., 1883-) (1990), 249(4970), 783–6.
16. Yuan, Y.; Hwang, E. S.; Altman, S. Targeted cleavage of mRNA by human RNase P. Proc. Natl. Acad. Sci. USA (1992) 89, 8006–10.
17. Harris, Michael E.; Pace, Norman R.. Identification of phosphates involved in catalysis by the ribozyme RNase P RNA. RNA (1995), 1(2), 210–18.
18. Pan, Tao; Loria, Andrew; Zhong, Kun. Probing of tertiary interactions in RNA: 2'-hydroxyl-base contacts between the RNase P RNA and pre-tRNA. Proc. Natl. Acad. Sci. U.S.A. (1995), 92(26), 12510–14.
19. Pyle, Anna Marie; Green, Justin B.. Building a Kinetic Framework for Group II Intron Ribozyme Activity: Quantitation of Interdomain Binding and Reaction Rate. Biochemistry (1994), 33(9), 2716–25.
20. Michels, William J. Jr.; Pyle, Anna Marie. Conversion of a Group II Intron into a New Multiple- Turnover Ribozyme that Selectively Cleaves Oligonucleotides: Elucidation of Reaction Mechanism and Structure/Function Relationships. Biochemistry (1995), 34(9), 2965–77.
21. Zimmerly, Steven; Guo, Huatao; Eskes, Robert; Yang, Jian; Perlman, Philip S.; Lambowitz, Alan M.. A group II intron RNA is a catalytic component of a DNA endonuclease involved in intron mobility. Cell (Cambridge, Mass.) (1995), 83(4), 529–38.
22. Griffin, Edmund A., Jr.; Qin, Zhifeng; Michels, Williams J., Jr.; Pyle, Anna Marie. Group II intron ribozymes that cleave DNA and RNA linkages with similar efficiency, and lack contacts with substrate 2'-hydroxyl groups. Chem. Biol (1995), 2(11), 761–70.
23. Michel, Francois; Ferat, Jean Luc. Structure and activities of group II introns. Annu. Rev. Biochem. (1995), 64, 435–61.
24. Abramovitz, Dana L.; Friedman, Richard A.; Pyle, Anna Marie. Catalytic role of 2'-hydroxyl groups within a group II intron active site. Science (Washington, D.C.) (1996), 271(5254), 1410–13.
25. Daniels, Danette L.; Michels, William J., Jr.; Pyle, Anna Marie. Two competing pathways for self-splicing by group II introns: a quantitative analysis of in vitro reaction rates and products. J. Mol. Biol. (1996), 256(1), 31–49.
26. Guo, Hans C. T.; Collins, Richard A.. Efficient trans-cleavage of a stem-loop RNA substrate by a ribozyme derived from Neurospora VS RNA. EMBO J. (1995), 14(2), 368–76.

TABLE 1-continued

Characteristics of naturally occurring ribozymes

27. Hampel, Arnold; Tritz, Richard; Hicks, Margaret; Cruz, Philip. 'Hairpin' catalytic RNA model: evidence for helixes and sequence requirement for substrate RNA. Nucleic Acids Res. (1990), 18(2), 299–304.
28. Chowrira, Bharat M.; Berzal-Herranz, Alfredo; Burke, John M.. Novel guanosine requirement for catalysis by the hairpin ribozyme. Nature (London) (1991), 354(6351); 320–2.
29. Berzal-Herranz, Alfredo; Joseph, Simpson; Chowrira, Bharat M.; Butcher, Samuel E.; Burke, John M.. Essential nucleotide sequences and secondary structure elements of the hairpin ribozyme. EMBO J. (1993), 12(6), 2567–73.
30. Joseph, Simpson; Berzal-Herranz, Alfredo; Chowrira, Bharat M.; Butcher, Samuel E.. Substrate selection rules for the hairpin ribozyme determined by in vitro selection, mutation, and analysis of mismatched substrates. Genes Dev. (1993), 7(1), 130–8.
31. Berzal-Herranz, Alfredo; Joseph, Simpson; Burke, John M.. In vitro selection of active hairpin ribozymes by sequential RNA-catalyzed cleavage and ligation reactions. Genes Dev. (1992), 6(1), 129–34.
32. Hegg, Lisa A.; Fedor, Martha J.. Kinetics and Thermodynamics of Intermolecular Catalysis by Hairpin Ribozymes. Biochemistry (1995), 34(48), 15813–28.
33. Grasby, Jane A.; Mersmann, Karin; Singh, Mohinder; Gait, Michael J.. Purine Functional Groups in Essential Residues of the Hairpin Ribozyme Required for Catalytic Cleavage of RNA. Biochemistry (1995), 34(12), 4068–76.
34. Schmidt, Sabine; Beigelman, Leonid; Karpeisky, Alexander; Usman, Nassim; Sorensen, Ulrik S.; Gait, Michael J.. Base and sugar requirements for RNA cleavage of essential nucleoside residues in internal loop B of the hairpin ribozyme: implications for secondary structure. Nucleic Acids Res. (1996), 24(4), 573–81.
35. Perrotta, Anne T.; Been, Michael D.. Cleavage of oligoribonucleotides by a ribozyme derived from the hepatitis .delta. virus RNA sequence. Biochemistry (1992), 31(1), 16–21.
36. Perrotta, Anne T.; Been, Michael D.. A pseudoknot-like structure required for efficient self-cleavage of hepatitis delta virus RNA. Nature (London) (1991), 350(6317), 434–6.
37. Puttaraju, M.; Perrotta, Anne T.; Been, Michael D.. A circular trans-acting hepatitis delta virus ribozyme. Nucleic Acids Res. (1993), 21(18), 4253–8.

TABLE II

2.5 μmol RNA Synthesis Cycle

| Reagent | Equivalents | Amount | Wait Time* |
|---|---|---|---|
| Phosphoramidites | 6.5 | 163 μL | 2.5 |
| S-Ethyl Tetrazole | 23.8 | 238 μL | 2.5 |
| Acetic Anhydride | 100 | 233 μL | 5 sec |
| N-Methyl Imidazole | 186 | 233 μL | 5 sec |
| TCA | 83.2 | 1.73 mL | 21 sec |
| Iodine | 8.0 | 1.18 mL | 45 sec |
| Acetonitrile | NA | 6.67 mL | NA |

*Wait time does not include contact time during delivery.

What is claimed is:

1. A ribozyme comprising at least one L-nucleotide substitution.

2. The ribozyme of claim 1, wherein said L-nucleotide has the formula I:

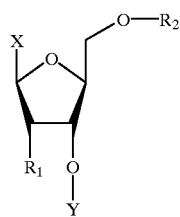

wherein, X is a nucleic acid base, which may be modified or unmodified, or H; Y is a phosphorus-containing group; $R_1$ is H, OH or other 2'-modifications; and $R_2$ is a blocking group or a phosphorus-containing group.

3. The ribozymne of claim 1, wherein said ribozyme has an endonuclease activity.

4. The ribozyme of claim 1, wherein said ribozyme is capable of cleaving a peptide linkage.

5. The ribozyme of claim 2, wherein said ribozyme cleaves a separate nucleic acid molecule.

6. The ribozyme of claim 1, wherein said ribozyme ligates separate nucleic acid molecules.

7. The ribozyme of claim 5, wherein said separate nucleic acid molecule is a ribonucleic acid molecule.

8. The ribozyme of claim 1, wherein said ribozyme consists of L-nucleotides at every position in the ribozyme.

9. The ribozyme of claim 3, wherein said ribozyme is in a hammerhead ribozyme motif.

10. The ribozyme of claim 3, wherein said ribozyme is in a hairpin ribozyme motif.

11. The ribozyme of claim 3, wherein said ribozyme is in a hepatitis delta virus, group I intron, group II intron, VS RNA or RNase P RNA motif.

12. The ribozyme of claim 1, wherein said ribozyme comprises at least two said L-nucleotide substitutions which may be same or different.

13. The ribozyme of claim 1, wherein said ribozyme comprises at least one D-nucleotide residue.

14. The ribozyme of claim 5, wherein said ribozyme comprises between 12 and 100 bases complementary to said separate nucleic acid molecule.

15. The ribozyme of claim 5, wherein said ribozyme comprises between 14 and 24 bases complementary to said separate nucleic acid molecule.

16. The ribozyme of claim 2, wherein said $R_1$ is OH.

17. The ribozyme of claim 2, wherein said $R_1$ is amino.

18. The ribozyme of claim 2, wherein said $R_1$ is alkoxy.

19. The ribozyme of claim 2, wherein said X is selected from the group consisting of adenine, guanine, uracil, and cytosine.

20. A mammalian cell comprising the ribozyme of claim 1.

21. The mammalian cell of claim 20, wherein said mammalian cell is a human cell.

22. A pharmaceutical composition comprising the ribozyme of claim 1.

23. A method for modulating expression of a gene in a mammalian cell by administering to said cell at least one ribozyme of claim 1.

24. A method of cleaving a separate nucleic acid molecule comprising, contacting the ribozyme of claim 1 with said separate nucleic acid molecule under conditions suitable for the cleavage.

25. The method of claim 24, wherein said cleavage is carried out in the presence of a divalent cation.

26. The method of claim 25, wherein said divalent cation is $Mg^{2+}$.

27. The ribozyme of claim 1, wherein said ribozyme is chemically synthesized.

28. The ribozyme of claim 9, wherein said L-nucleotide substitution is at positions 4, or 7 of said hammerhead ribozyme motif.

29. The ribozyme of claim 9, wherein said L-nucleotide substitution is at positions 4 and 7 of said hammerhead ribozyme motif.

30. The ribozyme of claim 9, wherein said L-nucleotide substitution is at the 3' terminal position of said hammerhead ribozyme motif.

* * * * *